United States Patent
Shozui et al.

(10) Patent No.: US 9,587,259 B2
(45) Date of Patent: Mar. 7, 2017

(54) ESCHERICHIA COLI CAPABLE OF PRODUCING 3-AMINO-4-HYDROXYBENZOIC ACID

(71) Applicant: AJINOMOTO CO., INC., Tokyo (JP)

(72) Inventors: Fumi Shozui, Kanagawa (JP); Yoshinori Tajima, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 5 days.

(21) Appl. No.: 14/467,459

(22) Filed: Aug. 25, 2014

(65) Prior Publication Data

US 2014/0364579 A1    Dec. 11, 2014

Related U.S. Application Data

(63) Continuation of application No. PCT/JP2013/051778, filed on Jan. 28, 2013.

(30) Foreign Application Priority Data

Feb. 29, 2012 (JP) .................. 2012-044452

(51) Int. Cl.
*C12P 13/00* (2006.01)
*C08G 73/22* (2006.01)
(Continued)

(52) U.S. Cl.
CPC ............ *C12P 13/005* (2013.01); *C08G 73/22* (2013.01); *C12N 9/1029* (2013.01); *C12N 9/88* (2013.01);
(Continued)

(58) Field of Classification Search
CPC ..... C12P 13/005; C12N 15/70; C12N 9/1025; C12N 9/88; C08G 73/22; C12Y 203/01118; C12Y 401/99
See application file for complete search history.

(56) References Cited

U.S. PATENT DOCUMENTS 8,076,111 B2    12/2011  Fukui et al.
8,093,346 B2 *   1/2012  Suzuki ................... C08G 73/22
                                                435/183
(Continued)

FOREIGN PATENT DOCUMENTS

EP        2857510 A1    4/2015
JP        2004-283163   10/2004
(Continued)

OTHER PUBLICATIONS

Josephy et al., N-hydroxyarylamine O-acetyltransferase-deficient *Escherichia coli* strains are resistant to the mutagenicity of nitro compounds., Biol Chem. (2002), vol. 383(6), pp. 977-982.*

(Continued)

*Primary Examiner* — Alexander Kim
(74) *Attorney, Agent, or Firm* — Shelly Guest Cermak; Cermak Nakajima & McGowan LLP

(57) ABSTRACT

The present invention provides a method for conveniently and inexpensively producing an amino-hydroxybenzoic acid-type compound such as 3-amino-4-hydroxybenzoic acid by utilizing *Escherichia coli* that is a bacterium commonly used for a production process by biosynthesis. Specifically, the present invention provides an *Escherichia coli* having an ability to produce 3-amino-4-hydroxybenzoic acid, which is modified to reduce an activity of N-hydroxyarylamine O-acetyltransferase (NhoA); a method for producing a 3-amino-4-hydroxybenzoic acid-type compound using such *Escherichia coli*; and the like.

11 Claims, 1 Drawing Sheet

(51) Int. Cl.
   C12N 15/70   (2006.01)
   C12N 9/88    (2006.01)
   C12N 9/10    (2006.01)
(52) U.S. Cl.
   CPC ...... C12N 15/70 (2013.01); C12Y 203/01118 (2013.01); C12Y 401/99 (2013.01)

(56) References Cited

U.S. PATENT DOCUMENTS

| | | |
|---|---|---|
| 8,247,201 B2 | 8/2012 | Tajima et al. |
| 8,367,371 B2 | 2/2013 | Tajima et al. |
| 8,497,104 B2 | 7/2013 | Tajima et al. |
| 2010/0112647 A1 | 5/2010 | Hara et al. |
| 2011/0137007 A1 | 6/2011 | Suzuki et al. |

FOREIGN PATENT DOCUMENTS

| | | |
|---|---|---|
| JP | 2008-029325 | 2/2008 |
| WO | WO2010/005099 | 1/2010 |

OTHER PUBLICATIONS

Suzuki et al. with Supplementary Data, Novel benzene ring biosynthesis from C(3) and C(4) primary metabolites by two enzymes., The Journal of Biological Chemistry (2006), vol. 281, pp. 36944-36951.*

Branden and Tooze, Introduction to Protein Structure (1999), 2nd edition, Garland Science Publisher, pp. 3-12.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Diaz, E., et al., "Biodegradation of Aromatic Compounds by *Escherichia coli*," Microbiol. Mol. Biol. Rev. 2001;65 (4):523-569.

Extended European Search Report for European Patent App. No. 13754464.9 (Jul. 31, 2015).

Stadtman, E. R., et al., "Feed-back Inhibition and Repression of Aspartokinase Activity in *Escherichia coli* and *Saccharomyces cerevisiae*," J. Biol. Chem. 1961;236(7)2033-2038.

Office Action from Chinese Patent App. No. 201380011332.3 (May 6, 2015).

Database GenBank, [online], Accession No. AB259663.1, <http://www.ncbi.nlm.nih.gov/nuccore/ab259663>, Nov. 30, 2006 uploaded, [retrieved on Feb. 19, 2013].

Database GenBank, [online], Accession No. AB530136.1, <http://www.ncbi.nlm.nih.gov/nuccore/296784935?sat=15&satkey=6187097>, May 25, 2010 uploaded, [retrieved on Feb. 19, 2013].

Noguchi, A., et al., "A copper-containing oxidase catalyzes C-nitrosation in nitrosobenzamide biosynthesis," Nat. Chem. Biol. 2010;6:641-643.

Rude, M. A., et al., "Production of Ansamycin Polyketide Precursors in *Escherichia coli*," J. Antibiot. 2006;59 (8):464-470.

Sikora, A. L., et al., "Kinetic and Chemical Mechanism of Arylamine N-Acetyltransferase from *Mycobacterium tuberculosis*," Biochem. 2008;47:10781-10789.

Suzuki, H., et al., "Novel Benzene Ring Biosynthesis from C3 and C4 Primary Metabolites by Two Enzymes," J. Biol. Chem. 2006;281(48):36944-36951.

Suzuki, H., et al., "Arylamine N-Acetyltransferase Responsible for Acetylation of 2-Aminophenols in *Streptomyces griseus*," J. Bacteriol. 2007;189(5):2155-2159.

Yamamura, E.-T., et al., "Purification and biochemical properties of an N-hydroxyarylamine O-acetyltransferase from *Escherichia coli*," Biochim. Biophys. Acta 2000;1475:10-16.

International Search Report for PCT Patent App. No. PCT/JP2013/051778 (Feb. 26, 2013).

* cited by examiner

FIG. 1(a) – (c)
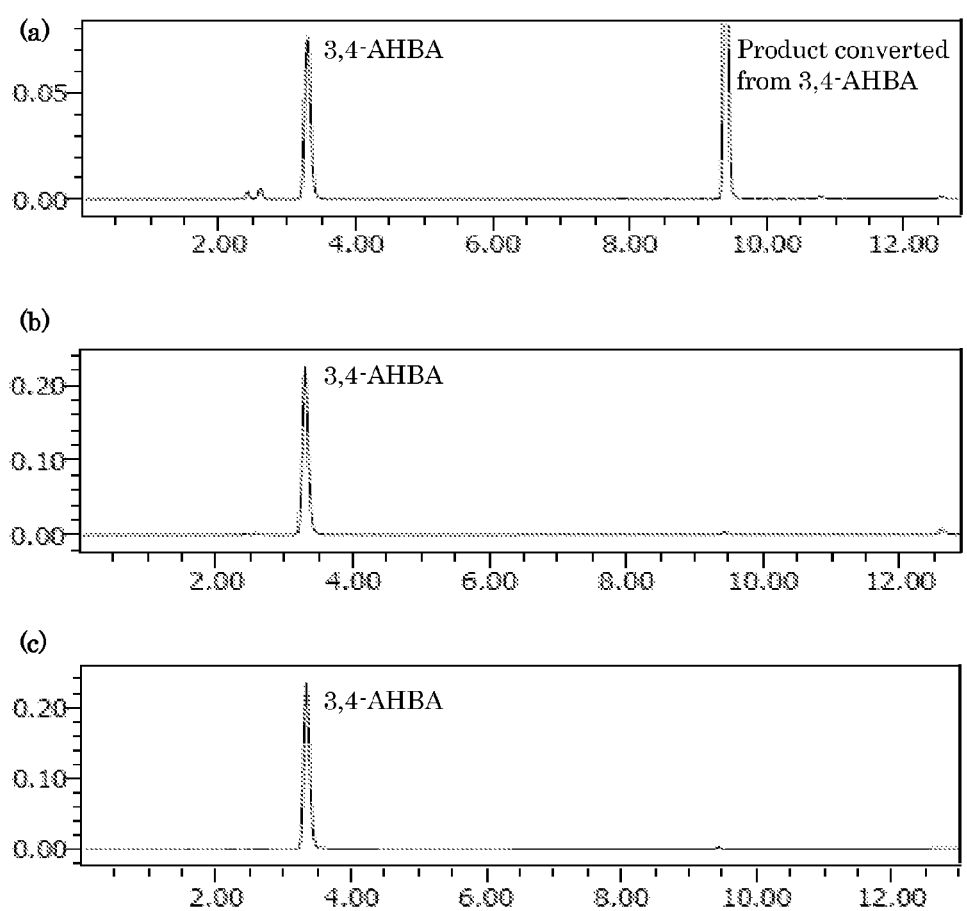

SEQUENCE LISTING

<160> NUMBER OF SEQ ID NOS: 18

<210> SEQ ID NO 1
<211> LENGTH: 270
<212> TYPE: PRT
<213> ORGANISM: Streptomyces griseus

<400> SEQUENCE: 1

```
Met Thr Leu Asp Leu Asp Ala Tyr Phe Ala Arg Ile Gly Trp Thr Gly
1               5                   10                  15

Asn Pro Arg Pro Thr Leu Glu Val Leu Arg Ser Leu His Arg Ala His
            20                  25                  30

Leu Ile Gly Ile Pro Phe Glu Asn Leu Glu Pro Val Leu Gly Ser Ala
        35                  40                  45

Pro Ser Leu Ala Leu Asp Asp Leu Glu Ala Lys Leu Val His Gly Gly
    50                  55                  60

Arg Gly Gly Tyr Cys Tyr Glu His Asn Thr Leu Phe Ser Ala Val Leu
65                  70                  75                  80

Arg Gln Ile Gly Phe Ser Val Thr Pro Leu Thr Ala Arg Val Val Leu
                85                  90                  95

Gly Ala Ala Pro Gly Asp Ile Arg Pro Arg Thr His Met Leu Met Arg
            100                 105                 110

Val Asp Val Ala Gly Glu Pro His Pro Tyr Leu Ala Asp Val Gly Phe
        115                 120                 125

Gly Ala Val Gly Ala Leu Leu Glu Pro Ile Glu Leu Val Glu Asp Ala
    130                 135                 140

Glu Leu Ser Asp Ala Pro Arg Arg His Arg Leu Val His Ala Pro His
145                 150                 155                 160

His Gly Pro Leu Pro Leu Trp Glu Leu Gln Ala Gly Gln Gly Gly Ser
                165                 170                 175

Trp Glu Pro Gln Tyr Asp Phe Thr Leu Asp Pro Tyr Glu Lys Pro Asp
            180                 185                 190

Tyr Glu Val Ile Asn Trp Phe Ile Ala Thr His Pro Arg Ser Pro Phe
        195                 200                 205

Arg Gln Ala Val Tyr Ala Gln Arg Thr Arg Ile Gly Ser His Leu Ala
    210                 215                 220

Leu Ser Gly Leu Asp Leu Val Glu Thr Ala Asp Asp Gly Thr Ile Arg
225                 230                 235                 240

Glu Arg Arg Leu Glu Asp Gly Asp Glu Ala Leu Arg Val Leu Thr Asp
                245                 250                 255

Asp Phe Gly Ile Arg Leu Pro Glu Gly Val Arg Leu Pro Glu
            260                 265                 270
```

<210> SEQ ID NO 2
<211> LENGTH: 281
<212> TYPE: PRT
<213> ORGANISM: Escherichia coli

<400> SEQUENCE: 2

```
Met Thr Pro Ile Leu Asn His Tyr Phe Ala Arg Ile Asn Trp Ser Gly
1               5                   10                  15

Ala Ala Ala Val Asn Ile Asp Thr Leu Arg Ala Leu His Leu Lys His
            20                  25                  30

Asn Cys Thr Ile Pro Phe Glu Asn Leu Asp Val Leu Leu Pro Arg Glu
        35                  40                  45

Ile Gln Leu Asp Asn Gln Ser Pro Glu Glu Lys Leu Val Ile Ala Arg
```

```
            50                  55                  60
Arg Gly Gly Tyr Cys Phe Glu Gln Asn Gly Val Phe Glu Arg Val Leu
 65                  70                  75                  80

Arg Glu Leu Gly Phe Asn Val Arg Ser Leu Leu Gly Arg Val Val Leu
                 85                  90                  95

Ser Asn Pro Pro Ala Leu Pro Pro Arg Thr His Arg Leu Leu Leu Val
                100                 105                 110

Glu Leu Glu Glu Glu Lys Trp Ile Ala Asp Val Gly Phe Gly Gly Gln
            115                 120                 125

Thr Leu Thr Ala Pro Ile Arg Leu Val Ser Asp Leu Val Gln Thr Thr
        130                 135                 140

Pro His Gly Glu Tyr Arg Leu Leu Gln Glu Gly Asp Asp Trp Val Leu
145                 150                 155                 160

Gln Phe Asn His His Gln His Trp Gln Ser Met Tyr Arg Phe Asp Leu
                165                 170                 175

Cys Glu Gln Gln Gln Ser Asp Tyr Val Met Gly Asn Phe Trp Ser Ala
                180                 185                 190

His Trp Pro Gln Ser His Phe Arg His His Leu Leu Met Cys Arg His
            195                 200                 205

Leu Pro Asp Gly Gly Lys Leu Thr Leu Thr Asn Phe His Phe Thr His
        210                 215                 220

Tyr Glu Asn Gly His Ala Val Glu Gln Arg Asn Leu Pro Asp Val Ala
225                 230                 235                 240

Ser Leu Tyr Ala Val Met Gln Glu Gln Phe Gly Leu Gly Val Asp Asp
                245                 250                 255

Ala Lys His Gly Phe Thr Val Asp Glu Leu Ala Leu Val Met Ala Ala
            260                 265                 270

Phe Asp Thr His Pro Glu Ala Gly Lys
        275                 280
```

<210> SEQ ID NO 3
<211> LENGTH: 399
<212> TYPE: DNA
<213> ORGANISM: Artificial Sequence
<220> FEATURE:
<223> OTHER INFORMATION: Ptac-Ttrp

<400> SEQUENCE: 3

```
ggtaccagat ctccctgttg acaattaatc atcggctcta taatgtgtgg aatcgtgagc      60
ggataacaat ttcacacaag gagactcccg ggagccgcca gttccgctgg cggcattttta    120
actttcttta atgaagccgg aaaaatccta aattcattta atatttatct ttttaccgtt    180
tcgcttaccc cggtcgaacg tcaacttacg tcatttttcc gcccaacagt aatataatca    240
aacaaattaa tcccgcaaca taacaccagt aaaatcaata attttctcta agtcacttat    300
tcctcaggta attgttaata tatccagaat gttcctcaaa atatattttc cctctatctt    360
ctcgttgcgc ttaatttgac taattctcat tagggatcc                            399
```

<210> SEQ ID NO 4
<211> LENGTH: 3383
<212> TYPE: DNA
<213> ORGANISM: Artificial Sequence
<220> FEATURE:
<223> OTHER INFORMATION: pSTV28-Ptac-Ttrp

<400> SEQUENCE: 4

```
cgtatggcaa tgaaagacgg tgagctggtg atatgggata gtgttcaccc ttgttacacc      60
```

```
gttttccatg agcaaactga aacgttttca tcgctctgga gtgaatacca cgacgatttc      120
cggcagtttc tacacatata ttcgcaagat gtggcgtgtt acggtgaaaa cctggcctat      180
ttccctaaag ggtttattga gaatatgttt ttcgtctcag ccaatccctg ggtgagtttc      240
accagttttg atttaaacgt ggccaatatg gacaacttct tcgcccccgt tttcaccatg      300
ggcaaatatt atacgcaagg cgacaaggtg ctgatgccgc tggcgattca ggttcatcat      360
gccgtttgtg atggcttcca tgtcggcaga atgcttaatg aattacaaca gtactgcgat      420
gagtggcagg gcggggcgta attttttttaa ggcagttatt ggtgcccctta aacgcctggt      480 gctacgcctg aataagtgat aataagcgga tgaatggcag aaattcgaaa gcaaattcga      540
cccggtcgtc ggttcagggc agggtcgtta aatagccgct tatgtctatt gctggtttac      600
cggtttattg actaccggaa gcagtgtgac cgtgtgcttc tcaaatgcct gaggccagtt      660
tgctcaggct ctccccgtgg aggtaataat tgacgatatg atcatttatt ctgcctccca      720
gagcctgata aaaacggtta gcgcttcgtt aatacagatg taggtgttcc acagggtagc      780
cagcagcatc ctgcgatgca gatccggaac ataatggtgc agggcgcttg tttcggcgtg      840
ggtatggtgg caggccccgt ggccggggga ctgttgggcg ctgccggcac ctgtcctacg      900
agttgcatga taaagaagac agtcataagt gcggcgacga tagtcatgcc ccgcgcccac      960
cggaaggagc taccggacag cggtgcggac tgttgtaact cagaataaga aatgaggccg     1020
ctcatggcgt tccaatacgc aaaccgcctc tccccgcgcg ttggccgatt cattaatgca     1080
gctggcacga caggtttccc gactggaaag cgggcagtga gcgcaacgca attaatgtga     1140
gttagctcac tcattaggca ccccaggctt tacactttat gcttccggct cgtatgttgt     1200
gtggaattgt gagcggataa caatttcaca caggaaacag ctatgaccat gattacgaat     1260
tcgagctcgg taccagatct ccctgttgac aattaatcat cggctctata atgtgtggaa     1320
tcgtgagcgg ataacaattt cacacaagga gactcccggg agccgccagt tccgctggcg     1380
gcattttaac tttctttaat gaagccggaa aaatcctaaa ttcatttaat atttatcttt     1440
ttaccgtttc gcttacccca gtcgaacgtc aacttacgtc attttccgc ccaacagtaa     1500 tataatcaaa caaattaatc ccgcaacata acaccagtaa aatcaataat tttctctaag     1560
tcacttattc ctcaggtaat tgttaatata tccagaatgt tcctcaaaat atattttccc     1620
tctatcttct cgttgcgctt aatttgacta attctcatta gggatcctct agagtcgacc     1680
tgcaggcatg caagcttggc actggccgtc gttttacaac gtcgtgactg ggaaaaccct     1740
ggcgttaccc aacttaatcg ccttgcagca catcccccctt tcgccagctg gcgtaatagc     1800
gaagaggccc gcaccgatcg cccttcccaa cagttgcgca gcctgaatgg cgaatgagct     1860
tatcgatgat aagctgtcaa acatgagaat acaacttat atcgtatggg gctgacttca     1920
ggtgctacat ttgaagagat aaattgcact gaaatctaga aatattttat ctgattaata     1980
agatgatctt cttgagatcg ttttggtctg cgcgtaatct cttgctctga aaacgaaaaa     2040
accgccttgc agggcggttt ttcgaaggtt ctctgagcta ccaactcttt gaaccgaggt     2100
aactggcttg gaggagcgca gtcaccaaaa cttgtccttt cagtttagcc ttaaccggcg     2160
catgacttca agactaactc ctctaaatca attaccagtg gctgctgcca gtggtgcttt     2220
tgcatgtctt tccgggttgg actcaagacg atagttaccg gataaggcgc agcggtcgga     2280
ctgaacgggg ggttcgtgca tacagtccag cttgagcga actgcctacc cggaactgag     2340
tgtcaggcgt ggaatgagac aaacgcggcc ataacagcgg aatgacaccg gtaaaccgaa     2400
```

-continued

```
aggcaggaac aggagagcgc acgagggagc cgccagggga aacgcctggt atctttatag    2460
tcctgtcggg tttcgccacc actgatttga gcgtcagatt tcgtgatgct tgtcagggg     2520
gcggagccta tggaaaaacg ctttgccgc ggccctctca cttccctgtt aagtatcttc     2580
ctggcatctt ccaggaaatc tccgccccgt tcgtaagcca tttccgctcg ccgcagtcga    2640
acgaccgagc gtagcgagtc agtgagcgag gaagcggaat atatcctgta tcacatattc    2700
tgctgacgca ccggtgcagc cttttttctc ctgccacatg aagcacttca ctgacaccct    2760
catcagtgcc aacatagtaa gccagtatac actccgctag cgctgatgtc cggcggtgct    2820
tttgccgtta cgcaccaccc cgtcagtagc tgaacaggag ggacagctga tagaaacaga    2880
agccactgga gcacctcaaa acaccatca tacactaaat cagtaagttg gcagcatcac     2940
ccgacgcact ttgcgccgaa taaatacctg tgacggaaga tcacttcgca gaataaataa    3000
atcctggtgt ccctgttgat accgggaagc cctgggccaa cttttggcga aaatgagacg    3060
ttgatcggca cgtaagaggt tccaactttc accataatga aataagatca ctaccgggcg    3120
tattttttga gttatcgaga ttttcaggag ctaaggaagc taaaatggag aaaaaaatca    3180
ctggatatac caccgttgat atatcccaat ggcatcgtaa agaacatttt gaggcatttc    3240
agtcagttgc tcaatgtacc tataaccaga ccgttcagct ggatattacg cctttttaa     3300
agaccgtaaa gaaaataag cacaagtttt atccggcctt tattcacatt cttgcccgcc     3360
tgatgaatgc tcatccggaa ttt                                            3383
```

<210> SEQ ID NO 5
<211> LENGTH: 274
<212> TYPE: PRT
<213> ORGANISM: Streptomyces griseus

<400> SEQUENCE: 5

```
Met Ala Pro Asn Ala Pro Phe Ala Arg Ser Leu Arg Leu Gln Arg Leu
1               5                   10                  15

His His His Asp Pro Asp Arg Leu Phe Ile Val Pro Leu Asp His Ser
            20                  25                  30

Ile Thr Asp Gly Pro Leu Ser Arg Ala His Arg Leu Asp Pro Leu Val
        35                  40                  45

Gly Glu Leu Ala Ser His His Val Asp Gly Ile Val Leu His Lys Gly
    50                  55                  60

Ser Leu Arg His Val Asp Pro Glu Trp Phe Thr Arg Thr Ser Leu Ile
65                  70                  75                  80

Val His Leu Ser Ala Ser Thr Val His Ala Pro Asp Pro Asn Ala Lys
                85                  90                  95

Tyr Leu Val Ser Ser Val Glu Glu Ser Leu Arg Met Gly Ala Asp Ala
            100                 105                 110

Val Ser Val His Val Asn Leu Gly Ser Glu Gly Glu Arg His Gln Ile
        115                 120                 125

Ala Asp Met Ala Ala Val Ala Glu Ala Cys Asp Arg Trp Asn Val Pro
    130                 135                 140

Leu Leu Ala Met Met Tyr Pro Arg Gly Pro Lys Ile Asp Asp Pro Arg
145                 150                 155                 160

Asp Pro Ala Leu Val Ala His Ala Val Gln Val Ala Val Asp Leu Gly
                165                 170                 175

Ala Asp Leu Val Lys Thr Leu Tyr Val Gly Ser Val Ala Ala Met Ala
            180                 185                 190

Glu Ile Thr Ala Ala Ser Pro Val Pro Val Val Val Val Gly Gly Pro
```

```
                195                 200                 205
Arg Asp Ser Asp Glu Ser Arg Ile Leu Ala Tyr Val Asp Asp Ala Leu
    210                 215                 220

Arg Gly Gly Ala Ala Gly Val Ala Met Gly Arg Asn Val Phe Gln Ala
225                 230                 235                 240

Pro Asp Pro Gly Ala Met Ala Asp Lys Leu Ser Asp Leu Ile His Asn
                245                 250                 255

Ser Gly Thr Arg Gly Ala Ala Arg Ala Pro Ala Gly Ala Ala Ala Gly
                260                 265                 270

Ala Ala

<210> SEQ ID NO 6
<211> LENGTH: 825
<212> TYPE: DNA
<213> ORGANISM: Streptomyces griseus

<400> SEQUENCE: 6
atggccccga acgcgccctt cgccaggagt ctgcgactcc agcggctcca tcaccacgac    60
cccgaccggc tgttcatcgt gccgctcgac cactcgatca ccgacggccc gctgagccgt   120
gcccaccgcc tcgacccgct cgtcggcgaa ctggcctccc accacgtcga cgggatcgtc   180
ctgcacaagg gctcgctgcg ccacgtggac ccggagtggt tcacgcggac ctcgctgatc   240
gtgcacctca cgccagcac cgtgcacgcg cccgacccga acgccaagta cctggtgtcg   300
agcgtcgagg agagcctgcg catgggcgcg gacgcggtga cgtccacgt caatctcggc   360 tccgagggg aacgccacca gatcgcggac atggcggcgg tcgcggaggc ctgcgaccgc   420
tggaacgtac cgctgctggc gatgatgtat ccgcgcggcc caagatcga cgacccgcgc   480 gatccggcgc tcgtcgccca tgccgtccag gtggccgtgg acctcggcgc cgacctggtc   540
aagacgctgt acgtcggatc ggtcgcggcg atggccgaga tcaccgcggc ctcgcccgtt   600
ccggtcgtcg tggtcggcgg accgcgcgac agtgacgaga gccggatcct cgcctacgtc   660
gacgacgcgc tgcgcggcgg cgcggccggt gtcgccatgg gccgcaacgt cttccaggcc   720
cctgatcccg gcgcgatggc ggacaagctc tccgacctca tccacaacag cggcaccagg   780
ggcgcggccc gggctccggc cggcgccgcc gccggagccg cctga                   825

<210> SEQ ID NO 7
<211> LENGTH: 396
<212> TYPE: PRT
<213> ORGANISM: Streptomyces griseus

<400> SEQUENCE: 7

Met Ser Ser Ser Pro Ser Pro Ser Ser Ser Ser Ser Ser
1               5                   10                  15

Ala Ser Ser Ser Ala Ser Ser Ser Pro Ser Ser Ser Ser Lys Leu Thr
                20                  25                  30

Trp Leu Asp Ile Arg Ser Val Gly Glu Ala Arg Ala Ala Ile Val Gln
            35                  40                  45

Glu Ala Leu His His Arg Val Glu Ala Leu Val Ala Asp Asp Pro Ala
        50                  55                  60

His Leu Ala Asp Leu Pro Thr Val Ala Lys Val Leu Leu Val Val
65                  70                  75                  80

Gly Lys Gln Ile Pro Glu Glu Phe Gly Glu Ala Thr Val Val Val
                85                  90                  95

Asp Pro Ser Lys His Gly Val Thr Pro Ala Glu Leu Ala Leu Lys His
```

```
            100                 105                 110
Pro Glu Ile Glu Phe Gly Arg Phe Val Glu Ile Ile Asp Ala Pro Thr
        115                 120                 125
Leu Glu Asp Ala Cys Glu Ser Ser Arg Thr Glu Lys Trp Ser Val Leu
130                 135                 140
Leu Phe Arg Asp Pro Thr Lys Ile Pro Leu Glu Ile Val Ile Ala Ala
145                 150                 155                 160
Ala Ala Arg Ala Ser Gly Ser Met Val Thr Ile Ala Gln Asp Leu Glu
                165                 170                 175
Glu Ala Glu Ile Leu Phe Gly Val Leu Glu His Gly Ser Asp Gly Val
                180                 185                 190
Met Met Ala Pro Lys Thr Val Gly Asp Ala Ala Glu Leu Lys Arg Ile
        195                 200                 205
Ala Glu Ala Gly Ile Pro Asn Leu Asn Leu Thr Glu Leu Arg Val Val
        210                 215                 220
Glu Thr Ser His Ile Gly Met Gly Glu Arg Ala Cys Val Asp Thr Thr
225                 230                 235                 240
Thr His Phe Gly Glu Asp Gly Ile Leu Val Gly Ser His Ser Lys
                245                 250                 255
Gly Met Ile Leu Cys Val Ser Glu Thr His Pro Leu Pro Tyr Met Pro
                260                 265                 270
Thr Arg Pro Phe Arg Val Asn Ala Gly Ala Ile His Ser Tyr Thr Leu
        275                 280                 285
Gly Arg Asp Glu Arg Thr Asn Tyr Leu Ser Glu Leu Lys Thr Gly Ser
        290                 295                 300
Lys Leu Thr Ala Val Asp Ile Lys Gly Asn Thr Arg Leu Val Thr Val
305                 310                 315                 320
Gly Arg Val Lys Ile Glu Thr Arg Pro Leu Ile Ser Ile Asp Ala Glu
                325                 330                 335
Ala Pro Asp Gly Arg Arg Val Asn Leu Ile Leu Gln Asp Asp Trp His
                340                 345                 350
Val Arg Val Leu Gly Pro Gly Gly Thr Val Leu Asn Ser Thr Glu Leu
        355                 360                 365
Lys Pro Gly Asp Thr Val Leu Gly Tyr Leu Pro Val Glu Asp Arg His
        370                 375                 380
Val Gly Tyr Pro Ile Asn Glu Phe Cys Leu Glu Lys
385                 390                 395

<210> SEQ ID NO 8
<211> LENGTH: 1191
<212> TYPE: DNA
<213> ORGANISM: Streptomyces griseus

<400> SEQUENCE: 8
atgtcttcgt ctccgtctcc gtctccgtcc tcgtcgtcct cgtcatctgc gtcctcgtcg      60
gcttcgtcgt cgccttcgtc gtcgtcgaag ctgacctggc tcgacatccg ttccgtgggc     120
gaggcccgtg ccgccatcgt ccaggaggcc ctgcaccacc gggtggaagc gctggtcgcc     180
gacgaccccg cccacctcgc ggacctgccg cccaccgtgg ccaaggtcct gctggtggtg     240
gggaagcaga tcccggagga gttcggcgag gcgacggtcg tcgtcgtcga cccgtcgaag     300
cacggtgtga cccccgccga actggcgctc aagcacccgg agatcgagtt cggcggttc     360 gtggagatca tcgacgcgcc gacgctggag gacgcctgcg agtcctcgcg gaccgagaag     420
tggtccgtcc tgctgttccg cgacccgacc aagatcccgc tggagatcgt gatcgccgcc     480
```

```
gccgcgcgcg cctccggttc gatggtgacc atcgcgcagg acctggagga ggcggagatc      540
ctcttcggcg tgctggagca cggctcggac ggcgtgatga tggccccgaa gacggtcggt      600
gacgccgccg agctgaagcg gatcgccgag gccggcatcc ccaacctcaa cctcaccgag      660
ctgcgcgtcg tggagaccag ccacatcggc atgggcgagc gggcctgcgt ggacaccacc      720
acgcatttcg gcgaggacga gggcatcctg gtcggctcgc actccaaggg catgatcctc      780
tgcgtcagcg agacccaccc gctgccgtac atgccgaccc ggccgttccg cgtcaacgcc      840
ggcgccatcc actcgtacac gctgggcagg gacgagcgca cgaactacct gagcgaactg      900
aagacgggca gcaagctcac cgccgtcgac atcaagggca caccggct ggtgaccgtg      960 ggccgcgtga agatcgagac ccgcccgctg atctccatcg acgccgaggc cccggacggc     1020
cggcgcgtca acctgatcct ccaggacgac tggcacgtcc gggtcctcgg ccccggtggc     1080
acggtcctca acagcaccga gctgaagccc ggcgacacgg tcctcggcta cctgcccgtc     1140
gaggaccgtc acgtcggcta cccgatcaac gagttctgcc tggagaagta g             1191

<210> SEQ ID NO 9
<211> LENGTH: 2480
<212> TYPE: DNA
<213> ORGANISM: Artificial Sequence
<220> FEATURE:
<223> OTHER INFORMATION: EcGriIH

<400> SEQUENCE: 9
gaattcgagc tcggtaccag atctccctgt tgacaattaa tcatcggctc tataatgtgt       60
ggaatcgtga gcggataaca atttcacaca aggagactcc catggccccg aatgccccgt      120
ttgctcgtag cctgcgcctg caacgcctgc accaccatga cccggatcgc ctgttcatcg      180
tcccgctgga tcatagcatt accgacggtc cgctgtctcg tgcacaccgc ctggatccgc      240
tggttggcga actggcaagc catcacgtcg acggcattgt gctgcataaa ggttctctgc      300
gtcacgtgga tccggaatgg tttacccgca cgtcactgat cgtgcatctg agtgcgtcca      360
cggttcacgc cccggatccg aacgcaaaat atctggttag ctctgtcgaa gaatccctgc      420
gtatgggcgc ggatgccgtt agtgtccatg tgaatctggg ctccgaaggt gaacgtcacc      480
agattgcaga tatggcagca gtcgcagaag cgtgcgaccg ttggaacgtt ccgctgctgg      540
cgatgatgta tccgcgtggt ccgaaaatcg atgacccgcg tgatccggcc ctggtggcgc      600
atgccgttca gtcgctgtg gatctgggcg cggacctggt taaaaccctg tacgtgggtt      660
cagttgcagc tatggcagaa attacggcag catcgccggt gccggtggtt gtcgtgggcg      720
gtccgcgtga ttcagacgaa tcgcgcatcc tggcctacgt tgatgacgca ctgcgtggcg      780
gtgcagctgg tgttgctatg ggtcgcaatg tcttccaggc accggatccg ggtgcaatgg      840
ctgataaact gagcgacctg atccacaatt caggtacccg tggtgctgcc cgtgctccgg      900
ctggtgccgc cgctggtgct gcgtgataac ccaggagact cgaatgtcaa gttcccgtc      960 accgtcaccg tcatcttctt cctcgtcaag tgcaagttcc agtgcctctt caagtccgtc     1020
aagttcaagt aaactgacct ggctggatat tcgtagcgtg ggtgaagcac gtgcagcaat     1080
cgttcaggaa gccctgcatc accgtgtcga agcactggtg gctgatgacc cggcacacct     1140
ggcagatctg ccgccgaccg tggcaaaagt tctgctggtt gtgggtaaac aaattccgga     1200
agaatttggc gaagcgacgg tcgtggttgt cgatccgtca aaacatggtg tgaccccggc     1260
agaactggct ctgaaacacc cggaaatcga atttggccgc ttcgttgaaa ttatcgatgc     1320
```

```
gccgacgctg gaagacgcct gcgaaagctc tcgcaccgaa aaatggtccg tgctgctgtt    1380
tcgtgatccg acgaaaattc cgctggaaat tgttatcgca gctgcggccc gtgccagtgg    1440
ttccatggtc accattgcac aggacctgga agaagctgaa atcctgttcg gcgttctgga    1500
acacggcagc gatggtgtta tgatggcacc gaaaaccgtc ggtgacgcag ctgaactgaa    1560
acgcattgcg gaagccggca tcccgaacct gaatctgacg gaactgcgcg tggttgaaac    1620
ctctcatatt ggcatgggtg aacgtgcgtg cgtggatacc acgacccatt ttggcgaaga    1680
cgaaggtatt ctggtcggct cacactcgaa gggtatgatc ctgtgtgtga gtgaaacgca    1740
tccgctgccg tatatgccga cccgtccgtt ccgtgtgaac gcaggtgcta tccactccta    1800
tacgctgggc cgtgatgaac gcaccaatta cctgagcgaa ctgaaaacgg gctctaaact    1860
gaccgccgtc gacattaagg gtaacacgcg tctggtcacc gtgggccgcg ttaaaatcga    1920
aacccgtccg ctgatttcaa tcgatgcaga agcaccggac ggtcgtcgcg tgaacctgat    1980
tctgcaagat gactggcatg ttcgtgtcct gggtccgggc ggtacggtgc tgaacagcac    2040
cgaactgaaa ccgggtgata ccgttctggg ctacctgccg gtcgaagatc gccatgtggg    2100
ctatccgatc aacgaatttt gtctggaaaa ataataaccc gggagccgcc agttccgctg    2160
gcggcatttt aactttcttt aatgaagccg gaaaatcct aaattcattt aatatttatc    2220
tttttaccgt ttcgcttacc ccggtcgaac gtcaacttac gtcattttc cgcccaacag    2280 taatataatc aaacaaatta atcccgcaac ataacaccag taaaatcaat aattttctct    2340
aagtcactta ttcctcaggt aattgttaat atatccagaa tgttcctcaa aatatatttt    2400
ccctctatct tctcgttgcg cttaatttga ctaattctca ttagggatcc tctagagtcg    2460
acctgcaggc atgcaagctt                                                 2480
```

<210> SEQ ID NO 10
<211> LENGTH: 5109
<212> TYPE: DNA
<213> ORGANISM: Artificial Sequence
<220> FEATURE:
<223> OTHER INFORMATION: pUC57- EcGri

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accagatctc    420
cctgttgaca attaatcatc ggctctataa tgtgtggaat cgtgagcgga taacaatttc    480
acacaaggag actcccatgg ccccgaatgc ccgtttgct cgtagcctgc gcctgcaacg    540
cctgcaccac catgacccgg atcgcctgtt catcgtcccg ctggatcata gcattaccga    600
cggtccgctc tcgtgcac accgcctgga tccgctggtt ggcgaactgg caagccatca    660
cgtcgacggc attgtgctgc ataaaggttc tctgcgtcac gtggatccgg aatggtttac    720
ccgcacgtca ctgatcgtgc atctgagtgc gtccacggtt cacgcccggg atccgaacgc    780
aaaatatctg gttagctctg tcgaagaatc cctgcgtatg ggcgcggatg ccgttagtgt    840
ccatgtgaat ctgggctccg aaggtgaacg tcaccagatt gcagatatgg cagcagtcgc    900
```

```
agaagcgtgc gaccgttgga acgttccgct gctggcgatg atgtatccgc gtggtccgaa    960
aatcgatgac ccgcgtgatc cggccctggt ggcgcatgcc gttcaagtcg ctgtggatct   1020
gggcgcggac ctggttaaaa ccctgtacgt gggttcagtt gcagctatgg cagaaattac   1080
ggcagcatcg ccggtgccgg tggttgtcgt gggcggtccg cgtgattcag acgaatcgcg   1140
catcctggcc tacgttgatg acgcactgcg tggcggtgca gctggtgttg ctatgggtcg   1200
caatgtcttc caggcaccgg atccgggtgc aatggctgat aaactgagcg acctgatcca   1260
caattcaggt acccgtggtg ctgcccgtgc tccggctggt gccgccgctg gtgctgcgtg   1320
ataacccagg agactcgaat gtcaagttcc ccgtcaccgt caccgtcatc ttcttcctcg   1380
tcaagtgcaa gttccagtgc ctcttcaagt ccgtcaagtt caagtaaact gacctggctg   1440
gatattcgta gcgtgggtga agcacgtgca gcaatcgttc aggaagccct gcatcaccgt   1500
gtcgaagcac tggtggctga tgacccggca cacctggcag atctgccgcc gaccgtggca   1560
aaagttctgc tggttgtggg taaacaaatt ccggaagaat tggcgaagc gacggtcgtg    1620
gttgtcgatc cgtcaaaaca tggtgtgacc ccggcagaac tggctctgaa cacccggaa    1680
atcgaatttg ccgcttcgt tgaaattatc gatgcgccga cgctggaaga cgcctgcgaa    1740
agctctcgca ccgaaaaatg gtccgtgctg ctgtttcgtg atccgacgaa aattccgctg   1800
gaaattgtta tcgcagctgc ggcccgtgcc agtggttcca tggtcaccat tgcacaggac   1860
ctggaagaag ctgaaatcct gttcggcgtt ctggaacacg gcagcgatgg tgttatgatg   1920
gcaccgaaaa ccgtcggtga cgcagctgaa ctgaaacgca ttgcggaagc cggcatcccg   1980
aacctgaatc tgacggaact cgcgtggtt gaaacctctc atattggcat gggtgaacgt   2040
gcgtgcgtgg ataccacgac ccattttggc gaagacgaag gtattctggt cggctcacac   2100
tcgaagggta tgatcctgtg tgtgagtgaa acgcatccgc tgccgtatat gccgacccgt   2160
ccgttccgtg tgaacgcagg tgctatccac tcctatacgc tgggccgtga tgaacgcacc   2220
aattacctga gcgaactgaa aacgggctct aaactgaccg ccgtcgacat taagggtaac   2280
acgcgtctgg tcaccgtggg ccgcgttaaa atcgaaaccc gtccgctgat ttcaatcgat   2340
gcagaagcac cggacggtcg tcgcgtgaac ctgattctgc aagatgactg gcatgttcgt   2400
gtcctgggtc cgggcggtac ggtgctgaac agcaccgaac tgaaaccggg tgataccgtt   2460
ctgggctacc tgccggtcga agatcgccat gtgggctatc cgatcaacga attttgtctg   2520
gaaaaataat aacccgggag ccgccagttc cgctggcggc attttaactt tcttttaatga   2580
agccggaaaa atcctaaatt catttaatat ttatcttttt accgtttcgc ttaccccggt   2640
cgaacgtcaa cttacgtcat ttttccgccc aacagtaata taatcaaaca aattaatccc   2700
gcaacataac accagtaaaa tcaataattt tctctaagtc acttattcct caggtaattg   2760
ttaatatatc cagaatgttc ctcaaaatat attttccctc tatcttctcg ttgcgcttaa   2820
tttgactaat tctcattagg gatcctctag agtcgacctg caggcatgca agcttggcgt   2880
aatcatggtc atagctgttt cctgtgtgaa attgttatcc gctcacaatt ccacacaaca   2940
tacgagccgg aagcataaag tgtaaagcct ggggtgccta atgagtgagc taactcacat   3000
taattgcgtt gcgctcactg cccgctttcc agtcggaaaa cctgtcgtgc cagctgcatt   3060
aatgaatcgg ccaacgcgcg gggagaggcg gtttgcgtat tgggcgctct tccgcttcct   3120
cgctcactga ctcgctgcgc tcggtcgttc ggctgcggcg agcggtatca gctcactcaa   3180
aggcggtaat acggttatcc acagaatcag gggataacgc aggaaagaac atgtgagcaa   3240
```

| | |
|---|---|
| aaggccagca aaaggccagg aaccgtaaaa aggccgcgtt gctggcgttt ttccataggc | 3300 |
| tccgccccc tgacgagcat cacaaaaatc gacgctcaag tcagaggtgg cgaaacccga | 3360 |
| caggactata agataccag gcgtttcccc ctggaagctc cctcgtgcgc tctcctgttc | 3420 |
| cgaccctgcc gcttaccgga tacctgtccg ccttctccc ttcgggaagc gtggcgcttt | 3480 |
| ctcatagctc acgctgtagg tatctcagtt cggtgtaggt cgttcgctcc aagctgggct | 3540 |
| gtgtgcacga accccccgtt cagcccgacc gctgcgcctt atccggtaac tatcgtcttg | 3600 |
| agtccaaccc ggtaagacac gacttatcgc cactggcagc agccactggt aacaggatta | 3660 |
| gcagagcgag gtatgtaggc ggtgctacag agttcttgaa gtggtggcct aactacggct | 3720 |
| acactagaag aacagtattt ggtatctgcg ctctgctgaa gccagttacc ttcggaaaaa | 3780 |
| gagttggtag ctcttgatcc ggcaaacaaa ccaccgctgg tagcggtggt ttttttgttt | 3840 |
| gcaagcagca gattacgcgc agaaaaaaag gatctcaaga agatcctttg atcttttcta | 3900 |
| cggggtctga cgctcagtgg aacgaaaact cacgttaagg gattttggtc atgagattat | 3960 |
| caaaaggat cttcacctag atccttttaa attaaaaatg aagttttaaa tcaatctaaa | 4020 |
| gtatatatga gtaaacttgg tctgacagtt accaatgctt aatcagtgag gcacctatct | 4080 |
| cagcgatctg tctatttcgt tcatccatag ttgcctgact ccccgtcgtg tagataacta | 4140 |
| cgatacggga gggcttacca tctggccca gtgctgcaat gataccgcga gacccacgct | 4200 |
| caccggctcc agatttatca gcaataaacc agccagccgg aagggccgag cgcagaagtg | 4260 |
| gtcctgcaac tttatccgcc tccatccagt ctattaattg ttgccgggaa gctagagtaa | 4320 |
| gtagttcgcc agttaatagt ttgcgcaacg ttgttgccat tgctacaggc atcgtggtgt | 4380 |
| cacgctcgtc gtttggtatg gcttcattca gctccggttc ccaacgatca aggcgagtta | 4440 |
| catgatcccc catgttgtgc aaaaaagcgg ttagctcctt cggtcctccg atcgttgtca | 4500 |
| gaagtaagtt ggccgcagtg ttatcactca tggttatggc agcactgcat aattctctta | 4560 |
| ctgtcatgcc atccgtaaga tgcttttctg tgactggtga gtactcaacc aagtcattct | 4620 |
| gagaatagtg tatgcggcga ccgagttgct cttgcccggc gtcaatacgg gataataccg | 4680 |
| cgccacatag cagaacttta aaagtgctca tcattggaaa acgttcttcg ggcgaaaac | 4740 |
| tctcaaggat cttaccgctg ttgagatcca gttcgatgta acccactcgt gcacccaact | 4800 |
| gatcttcagc atcttttact ttcaccagcg tttctgggtg agcaaaaaca ggaaggcaaa | 4860 |
| atgccgcaaa aaagggaata agggcgacac ggaaatgttg aatactcata ctcttccttt | 4920 |
| ttcaatatta ttgaagcatt tatcagggtt attgtctcat gagcggatac atatttgaat | 4980 |
| gtatttagaa aaataaacaa ataggggttc cgcgcacatt tccccgaaaa gtgccacctg | 5040 |
| acgtctaaga aaccattatt atcatgacat taacctataa aaataggcgt atcacgaggc | 5100 |
| cctttcgtc | 5109 |

```
<210> SEQ ID NO 11
<211> LENGTH: 39
<212> TYPE: DNA
<213> ORGANISM: Artificial Sequence
<220> FEATURE:
<223> OTHER INFORMATION: Primer 1

<400> SEQUENCE: 11
cacaaggaga ctcccatggc cccgaatgcc ccgtttgct                             39

<210> SEQ ID NO 12
<211> LENGTH: 45
```

```
<212> TYPE: DNA
<213> ORGANISM: Artificial Sequence
<220> FEATURE:
<223> OTHER INFORMATION: Primer 2

<400> SEQUENCE: 12
gaactggcgg ctcccgggtt attattttc cagacaaaat tcgtt              45

<210> SEQ ID NO 13
<211> LENGTH: 5411
<212> TYPE: DNA
<213> ORGANISM: Artificial Sequence
<220> FEATURE:
<223> OTHER INFORMATION: pSTV28- EcGri

<400> SEQUENCE: 13
cgtatggcaa tgaaagacgg tgagctggtg atatgggata gtgttcaccc ttgttacacc     60
gttttccatg agcaaactga aacgttttca tcgctctgga gtgaatacca cgacgatttc    120
cggcagtttc tacacatata ttcgcaagat gtggcgtgtt acggtgaaaa cctggcctat    180
ttccctaaag ggtttattga gaatatgttt ttcgtctcag ccaatccctg ggtgagtttc    240
accagttttg atttaaacgt ggccaatatg gacaacttct tcgcccccgt tttcaccatg    300
ggcaaatatt atacgcaagg cgacaaggtg ctgatgccgc tggcgattca ggttcatcat    360
gccgtttgtg atggcttcca tgtcggcaga atgcttaatg aattacaaca gtactgcgat    420
gagtggcagg gcggggcgta atttttttaa ggcagttatt ggtgccctta aacgcctggt    480
gctacgcctg aataagtgat aataagcgga tgaatggcag aaattcgaaa gcaaattcga    540
cccggtcgtc ggttcagggc agggtcgtta atagccgct tatgtctatt gctggtttac     600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccgacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg taccagatct ccctgttgac aattaatcat cggctctata atgtgtggaa   1320
tcgtgagcgg ataacaattt cacacaagga gactcccatg ccccgaatg ccccgtttgc    1380
tcgtagcctg cgcctgcaac gcctgcacca ccatgacccg gatcgcctgt tcatcgtccc   1440
gctggatcat agcattaccg acggtccgct gtctcgtgca caccgcctgg atccgctggt   1500
tggcgaactg gcaagccatc acgtcgacgg cattgtgctg cataaaggtt ctctgcgtca   1560
cgtggatccg gaatggttta cccgcacgtc actgatcgtg catctgagtg cgtccacggt   1620
tcacgccccg gatccgaacg caaaatatct ggttagctct gtcgaagaat ccctgcgtat   1680
gggcgcggat gccgttagtg tccatgtgaa tctgggctcc gaaggtgaac gtcaccagat   1740
tgcagatatg gcagcagtcg cagaagcgtg cgaccgttgg aacgttccgc tgctggcgat   1800
```

```
gatgtatccg cgtggtccga aaatcgatga cccgcgtgat ccggccctgg tggcgcatgc    1860
cgttcaagtc gctgtggatc tgggcgcgga cctggttaaa accctgtacg tgggttcagt    1920
tgcagctatg gcagaaatta cggcagcatc gccggtgccg gtggttgtcg tgggcggtcc    1980
gcgtgattca gacgaatcgc gcatcctggc ctacgttgat gacgcactgc gtggcggtgc    2040
agctggtgtt gctatgggtc gcaatgtctt ccaggcaccg gatccgggtg caatggctga    2100
taaactgagc gacctgatcc acaattcagg tacccgtggt gctgcccgtg ctccggctgg    2160
tgccgccgct ggtgctgcgt gataacccat gtcaagttcc ccgtcaccgt caccgtcatc    2220
ttcttcctcg tcaagtgcaa gttccagtgc ctcttcaagt ccgtcaagtt caagtaaact    2280
gacctggctg atattcgta gcgtgggtga agcacgtgca gcaatcgttc aggaagccct    2340
gcatcaccgt gtcgaagcac tggtggctga tgacccggca cacctggcag atctgccgcc    2400
gaccgtggca aaagttctgc tggttgtggg taaacaaatt ccggaagaat ttggcgaagc    2460
gacggtcgtg gttgtcgatc cgtcaaaaca tggtgtgacc ccggcagaac tggctctgaa    2520
acacccggaa atcgaatttg ccgcttcgt tgaaattatc gatgcgccga cgctggaaga    2580
cgcctgcgaa agctctcgca ccgaaaaatg gtccgtgctg ctgtttcgtg atccgacgaa    2640
aattccgctg gaaattgtta cgcagctgc ggcccgtgcc agtggttcca tggtcaccat    2700
tgcacaggac ctggaagaag ctgaaatcct gttcggcgtt ctggaacacg gcagcgatgg    2760
tgttatgatg gcaccgaaaa ccgtcggtga cgcagctgaa ctgaaacgca ttgcggaagc    2820
cggcatcccg aacctgaatc tgacggaact gcgcgtggtt gaaacctctc atattggcat    2880
gggtgaacgt gcgtgcgtgg ataccacgac ccatttggc gaagacgaag gtattctggt    2940
cggctcacac tcgaagggta tgatcctgtg tgtgagtgaa acgcatccgc tgccgtatat    3000
gccgacccgt ccgttccgtg tgaacgcagg tgctatccac tcctatacgc tgggccgtga    3060
tgaacgcacc aattacctga gcgaactgaa acgggctct aaactgaccg ccgtcgacat    3120
taagggtaac acgcgtctgg tcaccgtggg ccgcgttaaa atcgaaaccc gtccgctgat    3180
ttcaatcgat gcagaagcac cggacggtcg tcgcgtgaac ctgattctgc aagatgactg    3240
gcatgttcgt gtcctgggtc cgggcggtac ggtgctgaac agcaccgaac tgaaaccggg    3300
tgataccgtt ctgggctacc tgccggtcga agatcgccat gtgggctatc cgatcaacga    3360
attttgtctg gaaaataat aacccgggag ccgccagttc cgctggcggc attttaactt    3420
tctttaatga agccggaaaa atcctaaatt catttaatat ttatctttt accgtttcgc    3480
ttaccccggt cgaacgtcaa cttacgtcat ttttccgccc aacagtaata taatcaaaca    3540
aattaatccc gcaacataac accagtaaaa tcaataattt tctctaagtc acttattcct    3600
caggtaattg ttaatatatc cagaatgttc ctcaaaatat attttccctc tatcttctcg    3660
ttgcgcttaa tttgactaat tctcattagg gatcctctag agtcgacctg caggcatgca    3720
agcttggcac tggccgtcgt tttacaacgt cgtgactggg aaaaccctgg cgttacccaa    3780
cttaatcgcc ttgcagcaca tcccccttt gccagctggc gtaatagcga agaggcccgc    3840
accgatcgcc cttcccaaca gttgcgcagc ctgaatggcg aatgagctta tcgatgataa    3900
gctgtcaaac atgagaatta caacttatat cgtatgggc tgacttcagg tgctacattt    3960
gaagagataa attgcactga aatctagaaa tattttatct gattaataag atgatcttct    4020
tgagatcgtt ttggtctgcg cgtaatctct tgctctgaaa acgaaaaaac cgccttgcag    4080
ggcggttttt cgaaggttct ctgagctacc aactctttga accgaggtaa ctggcttgga    4140
ggagcgcagt caccaaaact tgtcctttca gtttagcctt aaccggcgca tgacttcaag    4200
```

-continued

```
actaactcct ctaaatcaat taccagtggc tgctgccagt ggtgcttttg catgtctttc    4260
cgggttggac tcaagacgat agttaccgga taaggcgcag cggtcggact gaacgggggg    4320
ttcgtgcata cagtccagct tggagcgaac tgcctacccg gaactgagtg tcaggcgtgg    4380
aatgagacaa acgcggccat aacagcggaa tgacaccggt aaaccgaaag gcaggaacag    4440
gagagcgcac gagggagccg ccaggggaaa cgcctggtat ctttatagtc ctgtcgggtt    4500
tcgccaccac tgatttgagc gtcagatttc gtgatgcttg tcaggggggc ggagcctatg    4560
gaaaaacggc tttgccgcgg ccctctcact tccctgttaa gtatcttcct ggcatcttcc    4620
aggaaatctc cgccccgttc gtaagccatt tccgctcgcc gcagtcgaac gaccgagcgt    4680
agcgagtcag tgagcgagga agcggaatat atcctgtatc acatattctg ctgacgcacc    4740
ggtgcagcct tttttctcct gccacatgaa gcacttcact gacaccctca tcagtgccaa    4800
catagtaagc cagtatacac tccgctagcg ctgatgtccg gcggtgcttt tgccgttacg    4860
caccaccccg tcagtagctg aacaggaggg acagctgata gaaacagaag ccactggagc    4920
acctcaaaaa caccatcata cactaaatca gtaagttggc agcatcaccc gacgcacttt    4980
gcgccgaata ataccctgtg acggaagatc acttcgcaga ataaataaat cctggtgtcc    5040
ctgttgatac cgggaagccc tgggccaact tttggcgaaa atgagacgtt gatcggcacg    5100
taagaggttc caactttcac cataatgaaa taagatcact accgggcgta ttttttgagt    5160
tatcgagatt ttcaggagct aaggaagcta aaatggagaa aaaaatcact ggatatacca    5220
ccgttgatat atcccaatgg catcgtaaag aacattttga ggcatttcag tcagttgctc    5280
aatgtaccta taaccagacc gttcagctgg atattacggc cttttttaaag accgtaaaga    5340 aaaataagca caagttttat ccggccttta ttcacattct tgcccgcctg atgaatgctc    5400
atccggaatt t                                                         5411
```

<210> SEQ ID NO 14
<211> LENGTH: 284
<212> TYPE: PRT
<213> ORGANISM: Streptomyces murayamaensis

<400> SEQUENCE: 14

```
Met Leu Thr His Ser Phe Ala Arg Lys Leu Arg Leu Arg Arg Leu His
1               5                   10                  15

Arg His Gly Gly Glu Arg Leu Leu Ile Val Pro Leu Asp His Ser Ile
            20                  25                  30

Thr Asp Gly Pro Val Thr Gly Gly Asn Arg Leu Asp His Leu Val Gly
        35                  40                  45

Gln Leu Ala Val Asn Gly Val Asp Ala Val Leu His Lys Gly Ser
    50                  55                  60

Leu Arg Tyr Val Asp Ser Ala Arg Phe Ala Arg Thr Ser Leu Ile Val
65                  70                  75                  80

His Leu Ser Ala Ser Thr Val His Ala Pro Asp Pro Asp Glu Lys Tyr
                85                  90                  95

Leu Val Ala Ser Val Glu Glu Cys Leu Arg Leu Gly Ala Asp Ala Val
            100                 105                 110

Ser Val His Val Asn Leu Gly Ser Ala Gln Glu Arg Gln Gln Ile Ala
        115                 120                 125

Asp Leu Ala Ala Val Gly Asp Ala Cys Asp Arg Trp Asn Val Pro Leu
    130                 135                 140

Leu Ala Met Met Tyr Pro Arg Gly Pro Lys Ile Thr Asn Pro Arg Asp
```

```
145                 150                 155                 160
Pro Ala Leu Ile Ala His Ala Ala Ser Leu Ala Ala Asp Leu Gly Ala
                165                 170                 175
Asp Ile Val Lys Thr Val Cys Ala Glu Thr Ile Gly Glu Met Arg Asp
            180                 185                 190
Ile Thr Ser Ala Ser Pro Val Pro Leu Val Val Gly Gly Pro Arg
        195                 200                 205
Glu Pro Asp Glu Lys Arg Val Leu Ala Tyr Val Asp Glu Ala Leu Arg
    210                 215                 220
Gly Gly Ala Ser Gly Val Ala Met Gly Arg Asn Val Phe Leu Ala Pro
225                 230                 235                 240
Asp Pro Gly Ala Met Ala Lys Val Ser Arg Leu Ile His Pro Ala
                245                 250                 255
Val Arg Arg Glu Val Pro Thr Asp His Val Pro Ala Pro Asn Ala Pro
            260                 265                 270
Ala Asp Asp Arg Thr Ala Pro Leu Thr Thr Val Ser
        275                 280

<210> SEQ ID NO 15
<211> LENGTH: 855
<212> TYPE: DNA
<213> ORGANISM: Streptomyces murayamaensis

<400> SEQUENCE: 15
atgttgaccc attccttcgc ccggaagctg cggctgcggc ggctgcaccg ccacggcggc      60
gagcggctgc tgatcgtgcc gctcgaccac tcgatcaccg acggaccggt gaccggcggc     120
aaccggctcg accatctggt ggggcagctc gccgtcaacg cgtggacgc cgtggtgctg     180 cacaagggca gcctgcgcta tgtcgactcg gcccggttcg cccgtacgtc gctgatcgtg     240
catctgagcg ccagcaccgt gcacgccccc gacccggacg agaagtacct ggtcgccagc     300
gtcgaggagt gcctgcggct gggcgcggac gcggtcagct gcacgtcaa cctcggttcc     360 gcccaggagc gccagcagat cgcggacctg gcggcggtcg cgacgcctg cgaccgctgg     420 aacgttccgc tgctcgccat gatgtatccg cgcggtccga agatcaccaa ccccgtgac     480 ccggcgctga tcgcccacgc ggcctcgctc gccgccgacc tgggcgccga catcgtcaag     540
accgtctgcg ccgagaccat cggcgagatg cgggacatca ccagcgcctc ccccgtcccg     600
ctcgtcgtgg tcggcggccc ccgcgagccc gacgagaagc gcgtgctcgc ctacgtggac     660
gaggcgctgc gcggcggcgc gtccggtgtc gcgatgggcc gcaacgtctt cctcgcgccg     720
gaccccggcg ccatggccgc caaggtgtcc cgcctgatcc accccgccgt acggcgcgag     780
gtgccgaccg accatgtgcc ggcgcccaac gcacccgccg atgaccgcac cgccccgttg     840
accaccgtct cttaa                                                      855

<210> SEQ ID NO 16
<211> LENGTH: 367
<212> TYPE: PRT
<213> ORGANISM: Streptomyces murayamaensis

<400> SEQUENCE: 16

Met Lys Ile Ser Trp Leu Asp Ala Arg Ser Leu Gly Asp Ala Lys Glu
1               5                  10                  15

Ala Ile Leu Gln Glu Ala Leu His Tyr Arg Leu Glu Gly Ile Val Ala
            20                  25                  30

Glu Asp Pro Ala Asp Phe Ala Asp Leu Pro Pro Thr Leu Thr Lys Val
```

```
                35                  40                  45
Leu Leu Pro Arg Lys Glu Leu Pro Ala Glu Phe Gly Asp Ala Ser Val
 50                  55                  60

Val Ile Val Asp Pro Thr Val His Gly Val Thr Pro Ala Glu Leu Ala
 65                  70                  75                  80

Leu Lys Tyr Pro Asp Ile Glu Phe Gly Arg Phe Val Glu Ile Ile Asp
                 85                  90                  95

Ala Pro Thr Leu Glu Asp Ala Cys Glu Ser Ala Arg Thr Glu Lys Trp
                100                 105                 110

Ser Val Leu Leu Phe Arg Asp Pro Thr Lys Ile Pro Leu Glu Ile Val
            115                 120                 125

Ile Ala Ala Ala Arg Ala Lys Gly Ser Met Ile Thr Val Ala Lys
130                 135                 140

Asp Val Glu Glu Ala Glu Ile Ile Phe Gly Val Leu Glu His Gly Ser
145                 150                 155                 160

Asp Gly Val Met Met Ala Pro Ala Ala Val Gly Asp Ala Ala Lys Leu
                165                 170                 175

Lys Ala Ala Ala Thr Ala Asp Val Pro Asp Leu Asp Leu Val Glu Leu
            180                 185                 190

Thr Val Glu Lys Thr Glu His Ile Gly Met Gly Glu Arg Ala Cys Val
        195                 200                 205

Asp Thr Cys Thr Tyr Phe Arg Glu Asp Glu Gly Ile Leu Val Gly Ser
210                 215                 220

His Ser Lys Gly Met Val Leu Cys Val Ser Glu Thr His Pro Leu Pro
225                 230                 235                 240

Tyr Met Pro Thr Arg Pro Phe Arg Val Asn Ala Gly Ala Ile His Ser
                245                 250                 255

Tyr Thr Leu Ser Lys Asp Glu Arg Thr Asn Tyr Leu Ser Glu Leu Lys
            260                 265                 270

Ala Gly Ser Lys Val Leu Ala Val Asp Ile Lys Gly Gln Thr Arg Leu
        275                 280                 285

Val Thr Val Gly Arg Val Lys Ile Glu Ser Arg Pro Leu Ile Ser Ile
290                 295                 300

Asp Ala Val Ala Pro Asn Gly Gln Arg Val Asn Leu Ile Leu Gln Asp
305                 310                 315                 320

Asp Trp His Val Arg Val Leu Gly Pro Gly Gly Val Val Leu Asn Ser
                325                 330                 335

Thr Glu Leu Lys Pro Gly Asp Thr Val Leu Gly Phe Leu Pro Ser Glu
            340                 345                 350

Asp Arg His Val Gly Tyr Pro Ile Asp Glu Phe Cys Leu Glu Lys
        355                 360                 365

<210> SEQ ID NO 17
<211> LENGTH: 1104
<212> TYPE: DNA
<213> ORGANISM: Streptomyces murayamaensis

<400> SEQUENCE: 17
atgaagatca gctggctcga cgcccgttcg ctcggcgacg ccaaggaggc catcctccag     60
gaggccctgc actaccgcct ggaaggcatc gtcgccgagg accccgccga cttcgccgac    120
ctgccgccga ccctcaccaa ggtgctgctg ccgcgcaagg agctgcccgc cgagttcggc    180
gacgcctccg tggtcatcgt ggacccgacc gtgcacggcg tgaccccggc cgaactcgcc    240
ctgaagtacc cggacatcga gttcggccgc ttcgtggaga tcatcgacgc gcccaccctt    300
```

```
gaggacgcct gcgagtcggc gcgcaccgag aagtggagcg tgctgctctt ccgcgacccc    360
accaagatcc cgctggagat cgtgatcgcg gcggccgccc gcgccaaggg cagcatgatc    420
acggtggcca aggacgtgga ggaggccgag atcatcttcg gcgtcctgga gcacggctcg    480
gacggcgtga tgatggcgcc ggcggcggtc ggcgacgcgg ccaagctgaa ggccgccgcc    540
accgccgacg tgcccgacct cgacctcgtc gagctcaccg tcgagaagac cgagcacatc    600
ggcatgggcg agcgcgcctg cgtcgacacc tgcacgtact tccgcgagga cgagggcatc    660
ctggtcggct cgcactccaa gggcatggtc ctgtgcgtca gcgagacgca cccgctgccg    720
tacatgccga cccggccgtt ccgggtcaac gcgggcgcga tccactcgta cacgctctcc    780
aaggacgagc ggaccaacta cctcagcgag ctgaaggcgg gcagcaaggt gctggccgtc    840
gacatcaagg gcagacgcg gctggtcacc gtcgggcggg tcaagatcga gtcccggccg    900
ctgatctcga tcgacgcggt ggcgccgaac gggcagcggg tgaatctgat tcttcaggac    960
gactggcacg tgcgggtgct cggccccggg ggtgtcgtgc tcaacagcac cgagctgaag    1020
ccgggggaca ccgttctggg gttcctgccc agcgaggacc ggcatgtcgg ttacccgatc    1080
gatgagttct gcctggagaa gtag                                          1104

<210> SEQ ID NO 18
<211> LENGTH: 846
<212> TYPE: DNA
<213> ORGANISM: Escherichia coli

<400> SEQUENCE: 18
atgacgccca ttctgaatca ctattttgcc cgtattaact ggtcgggagc tgctgcggtc     60
aatattgata cgcttcgtgc attgcacctg aaacacaatt gcaccattcc gtttgaaaac    120
ctcgacgttt tgctgccgag ggaaatacag cttgataatc aatcgccgga agagaaactg    180
gtgatagccc gtcgtggcgg ttactgtttt gagcagaatg gcgtgtttga gcgggtgtta    240
cgcgagctgg ggtttaacgt tcgcagcttg ttagggcgcg tagtgttatc aaatccgcca    300
gcattaccgc cgcgcaccca tcgtttgctg ttggtggaac tggaagagga aaaatggatt    360
gctgatgtcg gtttcggtgg gcagacgcta accgcgccga ttcgtttagt ttccgatctc    420
gtgcagacca cgccacacgg agagtatcgg ttgttgcagg agggtgatga ttgggtgttg    480
cagtttaatc atcatcagca ttggcagtcg atgtaccgtt ttgatctctg cgagcagcaa    540
caaagcgatt atgtgatggg caatttctgg tcggcgcact ggccgcagtc gcattttcgc    600
catcatttgc tgatgtgccg ccatttgccg gacggcggca agctgacact gaccaatttt    660
cattttaccc attatgaaaa tgggcacgcg gtggagcagc gaaatctacc ggatgtggcg    720
tcattatatg ctgtgatgca agaacagttt ggtctgggcg tggatgatgc gaaacatggc    780
tttaccgtgg atgagttagc gctggtgatg gcggcgtttg atacgcaccc ggaggcggga    840
aaataa                                                              846
```

ESCHERICHIA COLI CAPABLE OF PRODUCING 3-AMINO-4-HYDROXYBENZOIC ACID

CROSS-REFERENCE TO RELATED APPLICATIONS

This application is a Continuation of, and claims priority under 35 U.S.C. §120 to, International Application No. PCT/JP2013/051778, filed Jan. 28, 2013, and claims priority therethrough under 35 U.S.C. §119 to Japanese Patent Application No. JP 2012-044452 filed on Feb. 29, 2012, the entireties of which are incorporated herein by reference. Also, the Sequence Listing filed electronically herewith is hereby incorporated by reference (File name: 2014-08-25T_US-520_Seq_List; File size: 45 KB; Date recorded: Aug. 25, 2014.

BACKGROUND OF THE INVENTION

Field of the Invention

The present invention relates to an *Escherichia coli* bacterium having an ability to produce 3-amino-4-hydroxybenzoic acid and a method for producing an amino-hydroxybenzoic acid-type compound using the same.

Brief Description of the Related Art

Amino-hydroxybenzoic acid-type compounds are useful as intermediates in the manufacture of dyes, agricultural chemicals, pharmaceuticals, and other synthesized organic products, and as a monomer of a sophisticated and heat resistant polymer, polybenzoxazole. 3-Amino-4-hydroxybenzoic acid (3,4-AHBA) is biosynthesized in two steps using the enzymes GriI and GriH. GriI catalyzes a carbon-carbon binding reaction between a C4 compound having an amino group and a C3 or C4 compound. GriH catalyzes cyclization of a C7 compound or cyclization of a C8 compound with decarboxylation. Dihydroxyacetone phosphate (DHAP) and aspartate semialdehyde (ASA) are used as substrates in the biosynthesis.

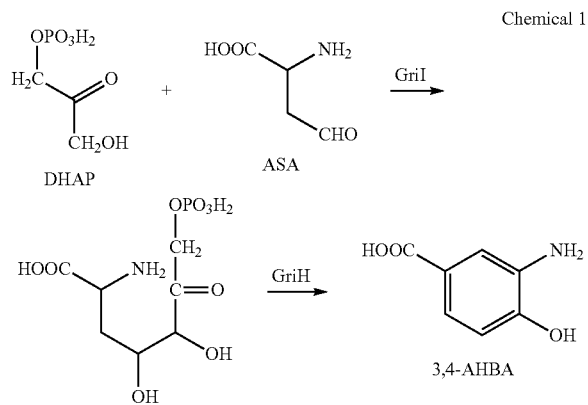

Chemical 1

In JP 2004-283163-A, a method for producing 3,4-AHBA using *Streptomyces griseus* into which griI and griH were introduced is disclosed. The document also discloses that 3-acetylamino-4-hydroxybenzoic acid (3,4-AcAHBA), which is a byproduct of 3,4-AHBA, is formed and that 3,4-AcAHBA is deacetylated to form 3,4-AHBA. Use of a strong base such as sodium hydroxide and a strong acid such as hydrochloric acid is exemplified as a specific method of deacetylating 3,4-AcAHBA. However, this method has a problem that the strong base and the strong acid have to be used.

In International Publication WO2010/005099, it is disclosed that 3,4-AHBA is formed by the use of *Corynebacterium glutamicum* into which griI and griH were introduced.

In Suzuki et al., J. Biol. Chem., 281 (2006), 36944-36951, it is disclosed that 3,4-AHBA and 3,4-AcAHBA are formed by introducing griI and griH into *Escherichia coli*.

In Suzuki et al., J. Bacteriol., 189 (2007), 2155-2159, it is disclosed that when an arylamine N-acetyltransferase gene (natA) is deleted in *Streptomyces griseus*, 3,4-AcAHBA is not formed in culture.

In Yamamura et al., Biochim. Biophys. Acta., 1475 (2000), 10-16, it is disclosed that an N-hydroxyarylamine O-acetyltransferase gene (nhoA) derived from *Escherichia coli* works to catalyze the acetylation of an aromatic amino group. Meanwhile, in Rude et al., J. Antibiot., vol. 59 (2006), p. 464, it is disclosed that *Escherichia coli* BAP1 strain forms an N-acetylated form (3,5-AcAHBA) as a byproduct of 3,5-AHBA (structural isomer of 3,4-AHBA). 3,5-AcAHBA is also produced as the byproduct in an nhoA gene-deleted strain (MAR1 strain) of *Escherichia coli* BAP1, and thus, the NhoA does not appear to be a major factor for N-acetylation of 3,5-AHBA.

SUMMARY OF THE INVENTION

It is an aspect of the present invention to provide a method for conveniently and inexpensively producing an aminohydroxybenzoic acid-type compound such as 3-amino-4-hydroxybenzoic acid by utilizing *Escherichia coli*. *Escherichia coli* is a bacterium commonly used for production processes by biosynthesis methods.

NhoA is involved in formation of 3,4-AcAHBA as a byproduct from 3,4-AHBA in *Escherichia coli*, and thus 3,4-AHBA, which is not acetylated, can be produced in large amounts by the use of a *Escherichia coli* bacterium modified to reduce an NhoA activity.

It is an aspect of the present invention to provide an *Escherichia coli* bacterium having an ability to produce 3-amino-4-hydroxybenzoic acid which has been modified to increase an activity of forming 3-amino-4-hydroxybenzoic acid from dihydroxyacetone phosphate and aspartate semialdehyde, wherein the *Escherichia coli* bacterium has been modified to reduce an N-hydroxyarylamine O-acetyltransferase (NhoA) activity.

It is a further aspect of the present invention to provide the *Escherichia coli* bacterium as described above, wherein the NhoA activity is reduced by mutating or deleting an nhoA gene on the chromosome.

It is a further aspect of the present invention to provide the *Escherichia coli* bacterium as described above, wherein the ability to produce 3-amino-4-hydroxybenzoic acid is conferred by being transformed with a recombinant vector incorporating a DNA encoding a protein having an activity of forming 3-amino-4-hydroxybenzoic acid from dihydroxyacetone phosphate and aspartate semialdehyde.

It is a further aspect of the present invention to provide the *Escherichia coli* bacterium as described above, wherein the protein having the activity of forming 3-amino-4-hydroxybenzoic acid is GriI and GriH.

It is a further aspect of the present invention to provide the *Escherichia coli* bacterium as described above, wherein the GriI is a protein according to any one of the following (A) to (C) and the GriH is a protein according to any one of the following (D) to (F):

(A) a protein comprising an amino acid sequence represented by SEQ ID NO:5 or SEQ ID NO:14;

(B) a protein comprising an amino acid sequence having one or several amino acid substitutions, deletions, insertions or additions in the amino acid sequence shown in (A) above, and having an aldolase activity;

(C) a protein comprising an amino acid sequence having 70% or more identity to the amino acid sequence represented in (A) above and having an aldolase activity;

(D) a protein comprising an amino acid sequence represented by SEQ ID NO:7 or SEQ ID NO:16;

(E) a protein comprising an amino acid sequence having one or several amino acid substitutions, deletions, insertions or additions in the amino acid sequence shown in (D) above, and having a 3-amino-4-hydroxybenzoic acid synthase activity; and (F) a protein comprising an amino acid sequence having 70% or more identity to the amino acid sequence shown in (D) above and having a 3-amino-4-hydroxybenzoic acid synthase activity.

It is a further aspect of the present invention to provide the *Escherichia coli* bacterium as described above, wherein the DNA encoding the protein having the activity of forming 3-amino-4-hydroxybenzoic acid comprises a griI gene and a griH gene.

It is a further aspect of the present invention to provide the *Escherichia coli* bacterium as described above, wherein the griI gene is a DNA according to any one of the following (a) to (c) and the griH gene is a DNA according to any one of the following (d) to (f):

(a) a DNA comprising a nucleotide sequence represented by SEQ ID NO:6 or SEQ ID NO:15;

(b) a DNA that hybridizes under a stringent condition with the nucleotide sequence complementary to the nucleotide sequence shown in (a) above and encodes a protein having an aldolase activity;

(c) a DNA having 70% or more identity to the nucleotide sequence shown in (a) above and having an aldolase activity;

(d) a DNA comprising a nucleotide sequence represented by SEQ ID NO:8 or SEQ ID NO:17;

(e) a DNA that hybridizes under a stringent condition with the nucleotide sequence complementary to the nucleotide sequence shown in (d) above and encodes a protein having a 3-amino-4-hydroxybenzoic acid synthase activity; and (f) a DNA having 70% or more identity to the nucleotide sequence shown in (d) above and having a 3-amino-4-hydroxybenzoic acid synthase activity.

It is a further aspect of the present invention to provide the *Escherichia coli* bacterium as described above, wherein the griI gene and the griH gene are derived from an actinomycete.

It is a further aspect of the present invention to provide the *Escherichia coli* bacterium as described above, wherein the griI gene and the griH gene are derived from the genus *Streptomyces*.

It is a further aspect of the present invention to provide the *Escherichia coli* bacterium as described above, wherein the griI gene and the griH gene are derived from *Streptomyces griseus*.

It is a further aspect of the present invention to provide the *Escherichia coli* bacterium as described above, wherein the griI gene and the griH gene are derived from *Streptomyces murayamaensis*.

It is a further aspect of the present invention to provide the *Escherichia coli* bacterium as described above, having a gene encoding a mutated aspartokinase III in which feedback inhibition is canceled.

It is a further aspect of the present invention to provide a method for producing a 3-amino-4-hydrozybenzoic acid-type compound, comprising a step of culturing the *Escherichia coli* bacterium as described above.

It is a further aspect of the present invention to provide a method for producing a polymer containing a 3-amino-4-hydrozybenzoic acid-type compound as a component, comprising a step of polymerizing the 3-amino-4-hydrozybenzoic acid-type compound produced by the method as described above.

It is a further aspect of the present invention to provide the method as described above, wherein the polymer is a polybenzoxazole polymer.

According to the present invention, the aminohydroxybenzoic acid-type compound such as 3-amino-4-hydroxybenzoic acid can be produced conveniently and inexpensively.

BRIEF DESCRIPTION OF DRAWINGS

FIG. 1(*a*)-(*c*) shows the results of analysis by reverse phase column chromatography for (a) a cultured supernatant of *Escherichia coli* BW25113 strain, (b) a cultured supernatant of *Escherichia coli* BW25113 ΔnhoA strain, and (c) a standard preparation of 3,4-AHBA.

DESCRIPTION OF THE PREFERRED EMBODIMENTS

The present invention provides an *Escherichia coli* bacterium that is able to produce 3-amino-4-hydroxybenzoic acid. Formation of an acetylated byproduct (3,4-AcAHBA) can be inhibited in the bacterium.

<1> Modification to Reduce Activity of N-Hydroxyarylamine O-Acetyltransferase (NhoA)

In the bacterium, the formation of the acetylated byproduct can be inhibited by modifying the bacterium to reduce the activity of N-hydroxyarylamine O-acetyltransferase (NhoA). The NhoA activity is an N-hydroxyarylamine O-acetyltransferase activity, and can mean an activity of forming 3-acetylamino-4-hydroxybenzoic acid (3,4-AcAHBA) from 3-amino-4-hydroxybenzoic acid (3,4-AHBA).

The phrase "modified to reduce the NhoA activity" can mean that the NhoA activity becomes lower than the specific activity in an unmodified strain, or a wild type *Escherichia coli*. The NhoA activity can be reduced to 50% or less, 30% or less, or 10% or less per microbial cell, as compared with that in the unmodified or wild-type strain. The activity can also be completely eliminated. It is only necessary that the NhoA activity is lower than that in the wild-type strain or the unmodified strain, but further accumulation of 3,4-AHBA is desirably enhanced compared with these strains. The phrase "modified to reduce the NhoA activity" can mean when the number of NhoA molecules per cell is decreased and also when the NhoA activity per molecule is reduced, and the like. Specifically, the modification to reduce the NhoA activity can be introduced by conventional mutagenesis or gene engineering treatment. Examples of the mutagenesis may include irradiation with X ray or ultraviolet ray and treatment with a mutagenic agent such as N-methyl-N'-nitro-N-nitrosoguanidine. Examples of such modification may include introducing a mutation into a nhoA gene (including an expression regulatory region) on a chromosome or deleting a part of or all of the nhoA gene so that the NhoA activity can be reduced or disappear compared with non-mutated strains. Examples of methods for mutating or deleting the gene may include modification of the expression regulatory region such as a promoter sequence and Shine-Dalgarno (SD) sequence, introduction of a miss-sense mutation, a nonsense mutation or a frameshift mutation into an open reading frame, as well as partial deletion of the gene (Qiu et al., J. Biol. Chem. 1997, 272 (13): 8611-7). The mutation or the deletion of the nhoA gene can be introduced into a microorganism by using a homologous recombination method in which a wild-type gene on a chromosome is replaced with a gene having a mutation or a deletion or by using a transposon or an IS factor. The homologous recombination method may include methods using a linear DNA, a temperature-sensitive plasmid and a non-replication plasmid. These methods are described in Datsenko et al., Proc. Natl. Acad. Sci. USA., 2000 Jun. 6; 97(12): 6640-5, U.S. Pat. No. 6,303,383, JP 05-007491-A, and the like.

Activity levels and a reduced activity of a target enzyme can be confirmed by measuring enzyme activity using a cell extract or a purified fraction obtained from a candidate microbial strain, and comparing the activity with that of a wild-type strain or an unmodified strain. For example, the NhoA activity can be measured by the method described in Biochim. Biophys. Acta., 1475 (2000), 10-16.

Escherichia coli modified to reduce the NhoA activity may include Escherichia coli inherently able to produce 3,4-AHBA, as well as Escherichia coli that is not inherently able to produce 3,4-AHBA but has been engineered to produce 3,4-AHBA. The ability to produce 3,4-AHBA can be engineered by a method described herein. Appropriate Escherichia coli strains can be used in the present invention, and examples thereof may include K12 strain (ATCC10798) or its substrains (e.g., BW25113 (CGSC7630), DH1 (ATCC33747), MG1655 (ATCC700926), W3110 (ATCC27325)), and B strain or its substrains (e.g., BL21 (ATCCBAA-1025), REL606 (CGSC12149)). Those that include the CGSC number can be obtained from The Coli Genetic Stock Center (cgsc.biology.yale.edu). Those that include with the ATCC number can be obtained from American Type Culture Collection (atcc.org).

NhoA may include a protein that includes an amino acid sequence having 70% or more, 80% or more, 90% or more, 95% or more, 98% or 99% or more identity to an amino acid sequence represented by SEQ ID NO:2 and having the NhoA activity. Also the nhoA gene may include a nucleotide sequence having 70% or more, 80% or more, 90% or more, 95% or more, 98% or 99% or more identity to a nucleotide sequence represented by SEQ ID NO:18 and encoding the protein having the NhoA activity.

Homology, that is, identity or similarity between the amino acid sequences or between the nucleotide sequences can be determined by using algorithm BLAST by Karlin and Altschul (Pro. Natl. Acad. Sci. USA, 90, 5873 (1993)) and FASTA by Pearson (Methods Enzymol., 183, 63 (1990)). Programs termed BLASTP and BLASTN were developed based on this algorithm BLAST (see ncbi.nlm.nih.gov). Thus, the homology between the amino acid sequences and between the nucleotide sequences may be calculated using these programs using the default settings. Also, for example, a numerical value obtained by calculating as a percentage using a full length portion of a polypeptide encoded in ORF using software GENETYX Ver. 7.0.9 with a setting of Unit Size to Compare=2, which is available from Genetyx Corporation employing Lipman-Pearson method may be used as the homology between the amino acid sequences. The lowest value in the values derived from these calculations may be employed as the homology between the amino acid sequences and between the nucleotide sequences.

The nucleotide sequence of the nhoA gene is sometimes different depending on the strain of Escherichia coli. Examples of the protein encoded by the nhoA gene may include proteins having an amino acid sequence having one or several amino acid substitutions, deletions, insertions or additions at one or multiple positions in the amino acid sequence represented by SEQ ID NO:2 and having the NhoA activity. Here, the term "several" can mean that the amino acid can vary depending on locations or the amino acid residues in a three dimensional structure of a protein, but can mean 1 to 50, 1 to 20, 1 to 10, or 1 to 5. Such a substitution, deletion, insertion addition or the like includes those due to a naturally occurring mutation (mutant or variant) based on individual difference of a microorganism having the nhoA gene.

The nhoA gene may also be DNA that hybridizes with a nucleotide sequence complementary to the nucleotide sequence represented by SEQ ID NO:18 under stringent conditions and encodes the protein having the NhoA activity. Here, the term "stringent conditions" refers to when a so-called specific hybrid is formed while a non-specific hybrid is not formed. One example is when polynucleotides having high homology (e.g., identity or similarity), for example 70% or more, 80% or more, 90% or more, 95% or more, or 98% or more homology hybridize while polynucleotides having lower homology than that do not hybridize. Specifically, such conditions may include hybridization in 6×SSC (sodium chloride/sodium citrate) at about 45° C. followed by one or two or more washings in 0.2×SSC and 0.1% SDS at 50 to 65° C.

<2> Modification to Increase Activity to Produce 3-amino-4-hydroxybenzoic Acid from Dihydroxyacetone Phosphate and Aspartate Semialdehyde A bacterium may be modified to increase the activity to produce 3-amino-4-hydroxybenzoic acid (3,4-AHBA) from dihydroxyacetone phosphate (DHAP) and aspartate semialdehyde (ASA). Such a modification can be accomplished by, for example, transforming the bacterium with a recombinant vector incorporating DNA encoding a protein having the activity to form 3,4-AHBA from DHAP and ASA. The protein having the activity to form 3,4-AHBA from DHAP and ASA is not particularly limited as long as the protein contributes to the formation of 3,4-AHBA from DHAP and ASA, and includes, for example, proteins having an enzyme activity to catalyze the formation of a carbon-carbon bond between DHAP and ASA (hereinafter sometimes abbreviated as an "aldolase activity"), and proteins having an enzyme activity to catalyze cyclization of a C7 compound obtained by forming the carbon-carbon bond between DHAP and ASA (hereinafter sometimes abbreviated as a 3-amino-4-hydroxybenzoic acid synthase activity). Hereinafter, both the above activities are sometimes referred to as the ability to biosynthesize 3,4-AHBA.

A gene encoding the protein having the enzyme activity to catalyze the formation of the carbon-carbon bond between DHAP and ASA may include a griI gene or a griI gene homolog (both the griI gene and the griI gene homolog are sometimes simply referred to as the griI gene) derived from Streptomyces griseus. The griI gene homolog refers to a gene that is derived from another microorganism, exhibits high homology to the above gene derived from Streptomyces griseus, and encodes a protein having the aldolase activity. Such a gene can be searched using BLAST. Example thereof may include an nspI gene derived from *Streptomyces murayamaensis* (SEQ ID NO:14 and 15), fructose-bisphosphate aldolase (Accession no. YP_483282) and fructose-bisphosphate aldolase (Accession no. YP_481172) derived from *Frankia* sp., fructose-bisphosphate aldolase derived from *Streptomyces scabies* (sanger.ac.uk/cgi-bin/blast/submitblast/s_scabies), fructose-bisphosphate aldolase (Accession no. Q39NQ9) derived from *Burkholderia* sp. 383, fructose-bisphosphate aldolase (Accession no. NP_247374) derived from *Methanococcus jannaschii*, and a dhn gene (Accession no. NC_000913) derived from *Escherichia coli* (Suzuki et al., Journal of Biological Chemistry vol. 281, NO. 48, pp. 36944-36951, supplementary data).

The gene encoding the protein having the enzyme activity to catalyze the cyclization of the C7 compound obtained by forming the carbon-carbon bond between DHAP and ASA may include a griH gene or a griH gene homolog (both the griH gene and the griH gene homolog are sometimes simply referred to as the griH gene) derived from *Streptomyces griseus*. The griH gene homolog refers to a gene that is derived from another microorganism, exhibits the high homology to the gene derived from *Streptomyces griseus*, and encodes the protein having the 3-amino-4-hydrosybenzoic acid synthase activity. Such a gene can be searched using BLAST. Examples thereof may include an nspH gene derived from *Streptomyces murayamaensis* (SEQ ID NO:16 and 17), 3-dehydroquinate synthase (Accession no. YP_483283) and 3-dehydroquinate synthase (Accession no. YP_481171) derived from *Frankia* sp., 3-dehydroquinate synthase (Accession no. YP_366552) and 3-dehydroquinate synthase (Accession no. YP_366553) derived from *Burkholderia* sp. 383, 3-dehydroquinate synthase derived from *Streptomyces scabies* (sanger.ac.uk/cgi-bin/blast/submitblast/s_scabies), and 3-dehydroquinate synthase (Accession no. NP_248244) derived from *Methanococcus jannaschii* (Suzuki et al, Journal of Biological Chemistry vol. 281, NO. 48, pp. 36944-36951, supplementary data).

GriI and GriH or the griI gene and the griH gene derived from any organism can be used in the present invention. For example, they may be derived from microorganisms such as the bacteria or actinomycetes described above. Examples of actinomycetes may include microorganisms belonging to genus *Streptomyces*. Examples of the microorganisms belonging to genus *Streptomyces* may include *Streptomyces griseus, Streptomyces murayamaensis, Streptomyces lividans*, and *Streptomyces scabies*. GriI and GriH, or the griI gene and the griH gene, may be derived from the same microorganism or different microorganisms.

The GriI homolog can include a protein having an amino acid sequence with 70% or more, 80% or more, 90% or more, 95% or more, or 98% or 99% or more identity to SEQ ID NO:5 or 14, a protein encoded by the above griI gene, and/or a protein having the aldolase activity. Examples thereof may include SEQ ID NOS:9, 11, 13, 15, 17, 19, and 21 in WO2010/005099. Also, the griI gene homolog can include a nucleotide sequence with 70% or more, 80% or more, 90% or more, 95% or more, or 98% or 99% or more identity to SEQ ID NO:6 or 15, and/or a griI gene and encoding the protein having aldolase activity. Examples thereof may include SEQ ID NOS:8, 10, 12, 14, 16, 18 and 20 in WO2010/005099.

The GriH homolog can include a protein having an amino acid sequence with 70% or more, 80% or more, 90% or more, 95% or more, or 98% or 99% or more identity to SEQ ID NO:7 or 16, a protein encoded by the above griH gene, and/or a protein having the 3-amino-4-hydroxybenzoic acid synthase activity. Examples thereof may include SEQ ID NOS:23, 25, 27, 29, 31, 33, and 35 in WO2010/005099. Also, the griH gene homolog can include a nucleotide sequence with 70% or more, 80% or more, 90% or more, 95% or more, or 98% or 99% or more identity to SEQ ID NO:8 or 17, and/or a griH gene encoding the protein having the 3-amino-4-hydroxybenzoiic acid synthase activity. Examples thereof may include SEQ ID NOS:22, 24, 26, 28, 30, 32, and 34 in WO2010/005099.

The person of ordinary skill in the art would readily be able to recognize position(s) in an amino acid sequence at which a mutation would have no effect on the activity of the protein, but a sequence alignment can be referenced regarding protein mutants. Specifically, those skilled in the art can (1) compare amino acid sequences of a plurality of homolog proteins, (2) determine relatively conserved regions and relatively not conserved regions, then (3) predict a region or regions that may or may not be functionally important from the relatively conserved regions and the relatively not conserved regions, respectively, and thus recognize correlativity of structures and functions. WO2010/005099 discloses the alignment of the amino acid sequence of the above griI gene homolog (FIGS. 1 and 2 in WO2010/005099), the alignment of the amino acid sequence of the above griH gene homolog (FIGS. 3 and 4 in WO2010/005099), and their consensus (common) sequence (SEQ ID NOS:36 and 37 in WO2010/005099). The above griI gene homolog includes a gene encoding an amino acid sequence represented by SEQ ID NO:36 in WO2010/005099, and the above griH gene homolog includes a gene encoding an amino acid sequence represented by SEQ ID NO:37 in WO2010/005099.

The homology (e.g., identity or similarity) between the amino acid sequences and between the nucleotide sequences can be determined as described above.

The nucleotide sequence of the griI gene or the griH gene may be different depending on the species and/or microbial strain of the chosen microorganism. Thus, the griI gene and the griH gene are only necessary to be able to enhance the ability to produce 3,4-AHBA in *Escherichia coli* by expressing them in *Escherichia coli*, e.g., augmenting their expression. For example, a protein that includes one or several amino acid substitutions, deletions, insertions additions or the like at one or multiple positions in the amino acid sequence of the protein encoded by the griI gene (SEQ ID NO:5 or 14) and having the aldolase activity is desirable as the protein encoded by the griI gene. Examples thereof may include SEQ ID NOS:9, 11, 13, 15, 17, 19, and 21 in WO2010/005099. A protein that includes one or several amino acid substitutions, deletions, insertions additions or the like at one or multiple positions in the amino acid sequence of the protein encoded by the griH gene (SEQ ID NO:7 or 16) and having the 3-amino-4-hydroxybenzoic acid synthase activity is desirable as the protein encoded by the griH gene. Examples thereof may include SEQ ID NOS:23, 25, 27, 29. 31, 33, and 35 in WO2010/005099. Here, the term "several" can mean that the amino acid can vary depending on the particular amino acid or the location of the amino acid in the three dimensional structure of a protein, but can be 1 to 50, 1 to 20, 1 to 10 or 1 to 5. Such an amino acid substitution, deletion, insertion addition or the like includes those due to naturally occurring mutation (mutant or variant) based on individual difference or species difference of the microorganism having the griI gene or the griH gene. The substitution can be a conservative substitution that is a neutral substitution in which a function is not affected. The conservative substitution is as described above.

Furthermore, degeneracy of the griI gene and the griH gene varies depending on the chosen host. Thus, codons may be replaced with codons available in *Escherichia coli*. Likewise, the griI gene and the griH gene may be genes encoding proteins that are extended or truncated on an N terminal side and/or a C terminal side as long as the gene has a function to enhance the ability to produce 3,4-AHBA in *Escherichia coli*. For example, a length of extended or truncated residues can be 50 or less, 20 or less, 10 or less or 5 or less of amino acid residues. More specifically, the gene may be a gene encoding a protein in which 50 to 5 amino acid residues on the N terminal side or 50 to 5 amino acid residues on the C terminal side have been extended or truncated.

Such a gene that is homologous to the griI gene or the griH gene can be acquired by, for example, modifying the gene encoding an amino acid sequence by site-specific mutagenesis so that an amino acid residue at a particular position of the encoded protein can include the substitution, deletion, insertion or addition. Such a homologous gene can also be acquired by conventionally known mutation treatments as follows. A method of treating the griI gene or the griH gene with hydroxylamine and the like in vitro and a method of treating a microorganism carrying the gene with ultraviolet ray or a mutating agent such as N-methyl-N'-nitro-N-nitrosoguanidine (NTG) or ethyl methanesulfonate (EMS) generally used for the mutation treatment, error prone PCR (Cadwell, R. C. PCR Meth. Appl. 2, 28 (1992)), DNA shuffling (Stemmer, W. P. Nature 370, 389 (1994)), and StEP-PCR (Zhao, H. Nature Biotechnol. 16, 258 (1998)) are available as mutation treatments. Utilizing these treatments, a mutation can be artificially introduced into the griI gene or the griH gene by gene recombination to acquire a gene encoding an enzyme with high activity.

The griI gene can also be DNA that hybridizes with a nucleotide sequence complementary to a nucleotide sequence of the griI gene or its homolog gene (e.g., SEQ ID NO:6 or 15, or SEQ ID NO:8, 10, 12, 14, 16, 18 or 20 in WO2010/005099) under stringent conditions and encodes the protein having the aldolase activity. The griH gene can also be DNA that hybridizes with a nucleotide sequence complementary to a nucleotide sequence of the griH gene or its homolog gene (e.g., SEQ ID NO:8 or 17, or SEQ ID NO:22, 24, 26, 28, 30, 32 or 34 in WO2010/005099) under stringent conditions and encodes the protein having the 3-amino-4-hydroxybenzoic acid synthase activity. The "stringent conditions" is the same as described above.

The descriptions concerning the above gene homologs and the conservative substitution are applied to the other genes described herein in the same manner.

Whether the griI gene and griH gene and their homologs do or do not encode the protein that enhances the ability to produce 3,4-AHBA can be confirmed by introducing these genes into a bacterium and the like having a gene encoding aspartokinase that is mutated so that feedback inhibition is canceled and examining whether the activity of forming 3,4-AHBA is enhanced or not. In such a case, the effect can be verified more clearly by quantifying 3,4-AHBA using reverse phase chromatography according to, for example, Suzuki, et al.'s method [J. Bio. Chem., 281, 823-833 (2006)].

<3> Recombinant Vector

A recombinant vector that can be used in the present invention can be obtained by introducing a desired gene into an expression vector. For example, when both the griI and the griH are used, they may be on separate recombinant vectors for transformation, or may be linked via an appropriate spacer on the same recombinant vector, as long as they are present in a transformant in an expressible state. The griI gene and the griH gene may be derived from the same microorganism or different microorganisms. When the griI gene and the griH gene are derived from the same microorganism and located in close proximity on a chromosome, a DNA fragment including both griI and griH may be cut out and carried on a vector.

The recombinant vector used in the present invention generally has a promoter, the aforementioned DNA of the present invention (e.g., griI and griH) and regulatory regions (operator and terminator) necessary for expression of the genes in *Escherichia coli* at appropriate positions so that they are functional.

The expression vector that can be used as the recombinant vector is not particularly limited, but must be able to function in *Escherichia coli*, and may be self-replicating, such as a plasmid, or may be integrated into the chromosome of a bacterium. Specifically, examples of the expression vector may include pSTV (e.g., pSTV28), pUC (e.g., pUC18, pUC19), pBR (e.g., pBR322), pHSG (e.g., pHSG298, pHSG299, pHSG399, pHSG398), pACYC (e.g., pACYC177, pACYC184), pMW (e.g., pMW118, pMW119, pMW218, pMW219), pQE (e.g., pQE) and derivatives thereof.

The promoter that can be used in the present invention is not particularly limited, and a promoter generally used for production of a foreign protein in *Escherichia coli* can be used. Examples thereof may include potent promoters such as a T7 promoter, a lac promoter, a trp promoter, a trc promoter, a tac promoter, a PR promoter and PL promoter of a lambda phage, a T5 promoter, and the like.

<4> Transformant

The bacterium of the present invention is not particularly limited as long as it is an *Escherichia coli* that is modified to have the ability to produce 3-amino-4-hydroxybenzoic acid and to reduce the activity of N-hydroxyarylamine O-acetyltransferase (NhoA), and can be a transformant. The transformant of the present invention can be obtained by using with a recombinant vector into which DNA encoding a protein having the activity of forming 3-amino-4-hydroxybenzoic acid from dihydroxyacetone phosphate and aspartate semialdehyde has been introduced.

The host *Escherichia coli* bacterium can be a strain that can efficiently supply dihydroxyacetone phosphate and aspartate semialdehyde, which are the substrates for biosynthesis of a 3-amino-4-hydroxybenzoic acid-type compound. *Escherichia coli* has aspartokinase III (AKIII) that is a non-coupled enzyme and works alone. AKIII in *Escherichia coli* in its native form is subject to feedback inhibition by lysine. The *Escherichia coli* of the present invention preferably has an AKIII gene having a mutation capable of canceling the feedback inhibition by lysine.

The mutation capable of canceling the feedback inhibition by an amino acid such as lysine has been reported for aspartokinase derived from various microorganisms such as *Escherichia coli*, *Corynebacterium glutamicum*, and *Serratia marcescens*. For example, the mutation of glutamic acid to lysine at position 250 (E250K), the mutation of methionine to isoleucine at position 318 (M318I), the mutation of threonine to methionine at position 344 (T344M), the mutation of serine to leucine at position 345 (S345L), and the mutation of threonine to isoleucine at position 352 (T352I) have been reported as mutations capable of canceling the feedback inhibition by lysine in AKIII in *Escherichia coli* (see e.g., Kikuchi et al., FEMS Microbiology Letters 173, 211-215 (1999), and Falco et al., BioTechnology 13, 577-582 (1995)). Therefore, *Escherichia coli* having the AKIII gene in which such a mutation has been introduced can be used in the present invention. Several amino acid residues are different even in wild-type AKIII depending on *Escherichia coli* strain from which the AKIII is derived, and such an allelic mutant may be used. The position to be modified for canceling the feedback inhibition in the allelic mutant can be identified by performing the sequence alignment publicly known to those skilled in the art. The modification to cancel the feedback inhibition in AKIII can be accomplished by a method known to those skilled in the art, e.g., by obtaining a mutant strain having resistance to a lysine analog such as 2-aminoethyl cysteine or by introducing site specific mutation by gene replacement utilizing homologous recombination. Also, *Escherichia coli* having an augmented activity of mutated AKIII in which the feedback inhibition was canceled can be obtained by transforming *Escherichia coli* with a plasmid containing a mutated AKIII gene in which the feedback inhibition was canceled.

The expression of a pyruvate carboxylase gene may further be augmented in *Escherichia coli* having the mutated AKIII in which the feedback inhibition was canceled.

According to methods known in the art, *Escherichia coli* can be transformed with a recombinant vector incorporating DNA encoding a protein having the activity of forming 3-amino-4-hydroxybenzoic acid from dihydroxyacetone phosphate and aspartate semialdehyde. For example, a protoplast method (Kiyoshi et al., Gene, 39, 281-286 (1985)), an electroporation method (Dunican et al., Bio/Technology, 7, 1067-1070 (1989)), and the like can be used. When transformation for canceling the feedback inhibition in AKIII is performed, either the transformation for conferring the activity of forming 3,4-AHBA or the transformation for canceling the feedback inhibition in AKIII may be performed in first.

<5> Methods for Producing 3-amino-4-hydroxybenzoic Acid-Type Compound and Polymer Including the Same The present invention also provides a method for producing a 3-amino-4-hydroxybenzoic acid-type compound, which includes a step of culturing the bacterium of the present invention.

The 3-amino-4-hydroxybenzoic acid-type compound in the present invention includes 3-amino-4-hydroxybenzoic acid (hereinafter sometimes abbreviated as "3,4-AHBA") having the following structure as well as a derivative and a salt thereof.

Chemical 2

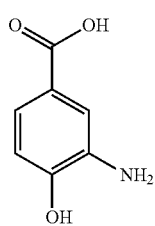

In the derivative of 3-amino-4-hydroxybenzoic acid, (1) at least one of the carboxyl group at position 1, the amino group at position 3, and/or the hydroxyl group at position 4 is derivatized, and/or (2) the carboxyl group at position 1, the amino group at position 3, and the hydroxyl group at position 4 are kept and a hydrogen atom on at least one carbon atom at positions 2, 5 and/or 6 is substituted with another atom or group. Examples of the other atom or group in (2) above may include halogen atoms (e.g., a fluorine atom, a bromine atom, a chlorine atom, an iodine atom), alkyl groups (e.g., alkyl groups having 1 to 6 carbon atoms such as methyl, ethyl, propyl, butyl, pentyl, and hexyl), a hydroxyl group, an alkyloxy group (the alkyl moiety is the same as described above), an amino group, a mono- or di-alkylamino group (the alkyl moiety is the same as described above), a cyano group, a nitro group, a sulfonyl group, and a carboxyl group. Specifically, examples of the derivative in (1) above may include derivatives in which the carboxyl group at position 1 is derivatized (e.g., 3-amino-4-hydroxybenzaldehyde in which the carboxyl group in 3-amino-4-hydroxybenzoic acid is aldehydated), derivatives in which the amino group at position 3 is derivatized with the group such as the above alkyl group (e.g., 3-alkylamino derivatives), and derivatives in which the hydroxyl group at position 4 is derivatized with the group such as the above alkyl group (e.g., 4-mono- or di-alkylamino derivatives).

Examples of salts include basic salts such as alkali metal (e.g., sodium, potassium, lithium) salts and alkali earth metal (e.g., calcium, magnesium) salts of carboxylic acid, and acid addition salts such as hydrochloride salts, sulfate salts, lead nitrate and phosphate salts.

The 3-amino-4-hydroxybenzoic acid-type compound can be produced by culturing the bacterium of the present invention and recovering the 3-amino-4-hydroxybenzoic acid-type compound produced in the medium.

The medium for culturing the bacterium of the present invention is not particularly limited as long as *Escherichia coli* is able to grow, and the bacterium can be cultured according to methods publicly known in the art. For example, the bacterium can be cultured in an ordinary medium containing a carbon source, a nitrogen source, and inorganic ions. Organic trace nutrients such as vitamins and amino acids may be added if necessary in order to obtain higher proliferation. A cultivation temperature is generally 25 to 42° C., and it is desirable to control pH to 5 to 8. A cultivation time period is generally 20 to 90 hours.

The cultivation of the bacterium of the present invention can be performed under conditions that control oxygen supply. Specifically, it is desirable to keep oxygen at 2.0 ppm or less when bacterial growth enters the logarithmic growth phase.

A recovery method used in steps of recovering and purifying the 3-amino-4-hydroxybenzoic acid-type compound from the culture medium can be appropriately selected from publicly known methods. For example, 3-amino-4-hydroxybenzoic acid-type compounds can be recovered from a culture medium supernatant obtained by removing microbial cells by centrifugation or membrane filtration after adjusting the pH of the culture medium to an acidic pH at which the solubility of the 3-amino-4-hydroxybenzoic acid-type compound is high. The recovery method of 3-amino-4-hydroxybenzoic acid from the culture medium supernatant can include purification by a porous adsorbent, crystallization and precipitation.

The porous adsorbent can be a porous solid adsorbent having a large surface area, and specifically includes hydrophilic adsorbents typified by silica gel, alumina, zeolite, bauxite, magnesia, activated white earth, acrylic synthetic adsorbents, and the like, and hydrophobic adsorbents typified by vegetable charcoal, bone charcoal, activated charcoal and aromatic synthetic adsorbents. Any adsorbent can be used without particular limitation as long as the purity of the 3-amino-4-hydroxybenzoic acid-type compound can be enhanced by adsorbing the impurities. In this regard, however, the impurities adsorbed by the porous adsorbent may contain abundant aromatic compounds mainly produced in the process of biochemical synthesis. Thus, the hydrophobic adsorbent typified by the activated charcoal and the aromatic synthetic adsorbent to which these compounds easily adsorb is suitably used in the present invention. These hydrophobic adsorbents may be used alone or in combination of two or more.

When the activated charcoal is used, its raw material is not particularly limited, and may include, but is not particularly limited to, plant raw materials such as wood powder and palm shell, coal/petroleum-based raw materials such as smokeless coal, petroleum pitch and cokes, synthetic resin-based raw materials such as acrylic resins, phenol resins, epoxy resins and polyester resins. The activated charcoal can be in the form of a powder, grain, and/or fibrous, and secondary processed articles such as filters and cartridges, and other forms that easily handled may be appropriately selected.

Meanwhile, when an aromatic synthetic adsorbent is used, the raw material thereof is not particularly limited, and for example, porous resins that can be used include 1) unsubstituted aromatic resins, 2) aromatic resins having a hydrophobic substituent(s), and 3) aromatic resins obtained by giving a special treatment to the unsubstituted aromatic resins. Specific compounds may include, for example, styrene- and divinylbenzene-based resins.

As mentioned above, an objective of contacting the 3-amino-4-hydroxybenzoic acid-type compound in the culture medium with the porous adsorbent is to adsorb the impurities to the porous adsorbent and to improve the purity of the 3-amino-4-hydroxybenzoic acid-type compound. However, 3-amino-4-hydroxybenzoic acid, which is an objective product, is sometimes adsorbed together in no small part with the impurities to the porous adsorbent. Thus, it is also possible to isolate and recover the 3-amino-4-hydroxybenzoic acid-type compound by contacting the 3-amino-4-hydroxybenzoic acid-type compound in the culture medium to the porous adsorbent, then contacting the porous adsorbent with a polar organic solvent to detach and dissolve the 3-amino-4-hydroxybenzoic acid-type compound in the polar organic solvent. The polar organic solvent used in the present invention refers to the organic solvent composed of polar molecules having a high dielectric constant, and can be used without particular limitation as long as the 3-amino-4-hydroxybenzoic acid-type compound can be detached from the porous adsorbent and the 3-amino-4-hydroxybenzoic acid-type compound can be dissolved in the polar organic solvent. The polar organic solvent may be used alone or in combination with two or more at a desired combination ratio.

Crystallization or the precipitation refers to a manipulation to produce a crystal or a precipitate, respectively, by evaporating the solvent in which an objective substance is dissolved to concentrate, or lowering the temperature, or keeping the concentration higher than a saturation solubility by adding a poor solvent to the solvent in which an objective substance is dissolved, and is not particularly limited including conventionally and publicly known methods. The produced crystal or precipitate can be separated by precipitation, filtration, centrifugation or the like.

The present invention also provides a method of producing a polymer that includes a 3-amino-4-hydroxybenzoic acid-type compound as a component. The production method of a polymer includes a step of polymerizing a 3-amino-4-hydroxybenzoic acid-type compound as at least one constituent of the polymer.

For example, the 3-amino-4-hydroxybenzoic acid-type compound that is purified from the culture medium of the bacterium of the present invention by using the porous adsorbent or by crystallization, precipitation or the like is polymerized by condensation polymerization in a non-oxidizing solvent acid such as methanesulfonic acid or polyphosphoric acid at high temperature (e.g., WO91/01304). In the production method of a polymer according to the present invention, the 3-amino-4-hydroxybenzoic acid-type compound may be polymerized with other constituents of a polymer. Examples of the other constituents include terephthalic acid and bisphenol A, or terephthalic acid and p-phenylenediamine. Known polymerizing method can be used as described in the following: U.S. Pat. Nos. 5,142,021, 5,219,981 and 5,422,416, and Kricheldorf et. al., (1992) Makromol. Chem., 193, 2467-2476, and Marcos-Fernandez et. al., (2001) Polymer, 42, 7933-7941. Examples of the polymer that includes a 3-amino-4-hydroxybenzoic acid-type compound which is produced by the method of the present invention include polybenzoxazole polymer, polyester and polyamide.

EXAMPLES

Embodiments of the present invention are further described with reference to the following non-limiting examples.

Example 1

Search for an Enzyme that Catalyzes Conversion of 3,4-AHBA in *Escherichia coli*

(1) Search for the 3,4-AHBA Conversion Enzyme Based on Genomic Information of *Escherichia coli*

It has been reported that arylamine N-acetyltransferase (convertible term: NatA; NCBI accession ID:BAF46971.1) catalyzes an N-acetylation reaction of 3,4-AHBA in *Streptomyces griseus* IFO13350 strain, and the amino acid sequence of NatA has been reported [Suzuki et. al., (2007) J. Bacteriol., 189, 2155-2159].

The amino acid sequence of NatA is shown in SEQ ID NO:1. In order to search for an enzyme having the same function as that of NatA, the genomic information of *Escherichia coli* K-12 strain was searched to find sequences with homology to the sequence of NatA. As a result of this search utilizing the published database (EcoCyc, ecocyc.org, Keseler et al., (2005) Nucleic Acids Res., 33, 334-337) and using BLASTP, it was found that N-hydroxyarylamine O-acetyltransferase (convertible term: NhoA, EC: 2.3.1.118, NCBI accession ID: NP_415980.1) in *Escherichia coli* K-12 strain exhibited 49% homology to NatA derived from *Streptomyces griseus* IFO13350 strain. The amino acid sequence of NhoA is shown in SEQ ID NO:2.

(2) Analysis of 3,4-AHBA Conversion Ability of nhoA Gene-Deleted Mutant Strain and Wild-Type Strain in *Escherichia coli*

*Escherichia coli* BW25113 ΔnhoA (same strain: JW1458, Keio Collection) was used as a strain having a deletion of a gene which codes NhoA (convertible term: nhoA, GenBank accession No.: NC_000913.2, GI: 947251). *Escherichia coli* BW25113 ΔnhoA strain was obtained by deleting the nhoA gene in *Escherichia coli* BW25113 strain (Haldimann et. al., (2001) J. Bacteriol., 183, 6384-6393) (CGSC7630) (Baba et. al., (2006) Mol. Syst. Biol., 2, 2006-2008). *Escherichia coli* BW25113 ΔnhoA strain is available from National Institute of Genetics (nig.ac.jp/). *Escherichia coli* BW25113 strain is available from The Coli Genetic Stock Center (cgsc.biology.yale.edu/).

The ability to convert 3,4-AHBA in *Escherichia coli* BW25113 ΔnhoA strain and BW25113 strain was calculated according to the following procedure. Microbial cells of each strain were uniformly applied onto an LB plate, and cultured at 37° C. for 24 hours. One loopful of the microbial cells from the resulting plate was inoculated in 4 mL of MS glucose/3,4-AHBA medium in a test tube, and cultured at 30° C. for 30 hours on a reciprocal shaking cultivation apparatus. A composition of the MS glucose/3,4-AHBA medium is as described in the following Table 1.

TABLE 1

Table 1. MS glucose/3,4-AHBA medium

| Components | Final concentration (g/L) |
|---|---|
| Glucose | 40 |
| $(NH_4)_2SO_4$ | 24 |
| 3,4-AHBA | 2 |
| $KH_2PO_4$ | 1 |
| $MgSO_4·7H_2O$ | 1 |
| $FeSO_4·7H_2O$ | 0.01 |
| $MnSO_4·7H_2O$ | 0.0082 |
| Yeast Extract | 2 |
| $CaCO_3$ | 50 |

The pH value of the medium was adjusted to 7.0 with KOH, and the medium was autoclaved at 120° C. for 20 minutes. Glucose and $MgSO_4.7H_2O$ were mixed and sterilized separately. $CaCO_3$ was added after dry heat sterilization. 3,4-AHBA was dissolved at 20 g/L in distilled water, then adjusted to pH 7.0 with KOH, sterilized through a filter, and subsequently added at a final concentration of 2.0 g/L.

After completion of the cultivation, an optical density (OD) value of the culture medium was measured using a spectrophotometer (HITACHI U-2900) at 600 nm. 3,4-AHBA in a culture supernatant was separated using reverse phase column chromatography, and its concentration was quantified (Suzuki et. al., (2006) J. Biol. Chem., 281, 36944-36951). The OD value at 600 nm, the concentration of 3,4-AHBA in the culture supernatant, and a conversion rate of 3,4-AHBA obtained from each microbial strain are shown in Table 2. The conversion rate of 3,4-AHBA was calculated using the following formula:

Conversion rate of 3,4-AHBA (%)]=100×{2 (g/L)−
[Concentration of 3,4-AHBA in culture medium
supernatant after completion of cultivation
(g/L)]}/2 (g/L)

TABLE 2

Table 2. Effect of nhoA deletion on ability to convert 3,4-AHBA

| Strain name | OD (600 nm) | Concentration of 3,4-AHBA (g/L) | Conversion rate of 3,4-AHBA (%) |
|---|---|---|---|
| BW25113 | 34.3 ± 0.4 | 0.60 ± 0.10 | 70 |
| BW25113ΔnhoA | 36.7 ± 1.0 | 1.80 ± 0.10 | 10 |

As a result, the concentration of 3,4-AHBA in the culture supernatant after the cultivation of *Escherichia coli* BW25113 strain was decreased by 30% of the initial concentration. On the other hand, the decrease of the 3,4-AHBA concentration in the culture supernatant after the cultivation in *Escherichia coli* BW25113 ΔnhoA strain was around 10%. Therefore, it was strongly suggested that NhoA catalyzed the conversion reaction of 3,4-AHBA.

Charts of the reverse phase column chromatography for the culture supernatant of *Escherichia coli* BW25113 strain, the culture supernatant of *Escherichia coli* BW25113 ΔnhoA strain, and a 3,4-AHBA standard preparation (supplied from Tokyo Chemical Industry CO., Ltd., Cat. No.: A0859) are shown in FIG. 1. These results suggest that 3,4-AHBA was converted to a compound detected at a retention time (R.T.) of 9.5 minutes in *Escherichia coli* BW25113 strain.

(3) Identification of Molecular Weight of Product Converted from 3,4-AHBA (R.T., 9.5 Minutes)

The molecular weight of the product converted from 3,4-AHBA (R.T., 9.5 minutes) described in Example 1(2) and present in the culture supernatant after the cultivation of BW25113 strain was identified by LC/MS. The analysis conditions are as follows.

Column: Inertsil ODS-3 2 μm 2.1×75 mm (supplied from GL Science)
Mobile phase: A=0.1% formic acid/$H_2O$
B=0.1% formic acid/acetonitrile
Gradient program: 0 minute: A/B=100/0
3 minutes: A/B=100/0
23 minutes: A/B=20/80
25 minutes: A/B=20/80
Flow rate: 0.2 mL/minute
Column temperature: room temperature (25° C.)
Detection wavelength: 254 nm (PDA)
MS ionization mode: ESI
Analysis machine model: Agilent Infinity1290 (LC)
Agilent Quadrupole LC/MS 6130 (MS)

As a result of the analysis, the m/z value of the converted product (R.T., 9.5 minutes) was 195.1, which is consistent with a calculated m/z value of an acetylated product of 3,4-AHBA (195.1). Hereinafter, this converted product (R.T., 9.5 minutes) is referred to as 3,4-AcAHBA.

Example 2

Construction of Bacteria Producing 3,4-AHBA by Introducing 3,4-AHBA Synthetase Gene Group Derived from *Streptomyces griseus* and Evaluation of Amounts of Accumulated 3,4-AHBA and 3,4-AcAHBA Construction of Plasmid pSTV28-Ptac-Ttrp for Expression Subsequently, the effect of nhoA deletion on accumulation of 3,4-AHBA was verified in a 3,4-AHBA producing bacteria. First, the expression plasmid pSTV28-Ptac-Ttrp was constructed for the purpose of producing 3,4-AHBA.

To begin with, a DNA fragment was chemically synthesized that includes a tac promoter (convertible term: Ptac) region (deBoer, et al., (1983) Proc. Natl. Acad. Sci. U.S.A., 80, 21-25) and a terminator (convertible term: Ttrp) region of a tryptophan operon derived from *Escherichia coli* (Wu et al., (1978) Proc. Natl. Acad. Sci. U.S.A., 75, 5442-5446), and also having a KpnI site at the 5' terminus and a BamHI site at the 3' terminus (the nucleotide sequence is shown as SEQ ID NO:3). The resulting DNA fragment was digested with KpnI and BamHI to obtain a DNA fragment containing Ptac and Ttrp. The purified DNA fragment and pSTV28 (supplied from Takara Bio Inc.) digested with KpnI and BamHI were ligated by a ligation reaction using DNA ligase. The resulting plasmid was designated as pSTV28-Ptac-Ttrp (the nucleotide sequence is shown as SEQ ID NO:4). An objective gene can be expressed and amplified by cloning the objective gene downstream of Ptac in this plasmid.

(2) Chemical Synthesis of griI Gene and griH Gene (griIH Gene) Corresponding to Codon Usage in *Escherichia coli*

It has been reported that synthesis of 3,4-AHBA is catalyzed by a 3,4-AHBA synthetase group consisting of aldolase (convertible term: SGR_4249, GriI) and 3,4-AHBA synthase (convertible term: SGR_4248, GriH) in *Streptomyces griseus* IFO13350 strain, and sequences of the genes encoding these enzymes have been reported (Suzuki et. al., (2006) J. Biol. Chem., 281, 36944-36951). GriI is encoded by the griI gene (GenBank accession no. AB259663.1, nucleotides: 13956 to 14780; GI: 117676060). The amino acid sequence of the GriI protein and a nucleotide sequence of the griI gene are shown as SEQ ID NO:5 and SEQ ID NO:6, respectively. GriH is encoded by the griH gene (GenBank accession no. AB259663.1, nucleotides: 12690 to 13880; GI: 117676059). The amino acid sequence of the GriH protein and the nucleotide sequence of the griH gene are shown as SEQ ID NO:7 and SEQ ID NO:8, respectively.

In order to efficiently express the griI gene and the griH gene in *Escherichia coli*, a sequence was designed so as to correspond to the codon usage in *Escherichia coli* by changing the sequences of the griI gene and the griH gene and to express as an operon, and this sequence was designated as EcGriIH. A DNA fragment was chemically synthesized by adding an EcoRI restriction enzyme recognition sequence to the 5' terminus and a HindIII restriction enzyme recognition sequence to the 3' terminus of EcGriIH (the sequence is shown as SEQ ID NO:9). EcGriIH, both termini of which the restriction enzyme recognition sequence had been added to, was digested with EcoRI and HindIII, and then cloned into pUC57 (supplied from GenScript) which had been digested with the same enzymes. The resulting vector was designated as pUC57-EcGri. The full length sequence of pUC57-EcGri is shown as SEQ ID NO:10.

(3) Construction of Plasmid for Expressing the griI Gene and griH Gene (griIH Gene)

An expression plasmid for expressing the griI gene and the griH gene in *Escherichia coli* was constructed using the following procedure. PCR was performed with pUC57-EcGri as a template using a synthesized oligonucleotide represented by SEQ ID NO:11 and further a synthesized oligonucleotide represented by SEQ ID NO:12 as primers and using PrimeStar GXL polymerase (supplied from Takara Bio Inc.). A reaction solution was prepared according to a composition attached to the kit, and a reaction at 98° C. for 10 seconds, 55° C. for 15 seconds and 68° C. for 150 seconds was performed in 30 cycles. As a result, a PCR product of about 2.1 kbp containing the EcGriIH gene fragment was obtained. Subsequently, the purified EcGriIH gene fragment and pSTV28-Ptac-Ttrp digested with SmaI were ligated using In-Fusion HD Cloning Kit (supplied from Clontech). The resulting plasmid for expressing the griIH gene was designated as pSTV28-EcGri. A full length sequence of pSTV28-EcGri is shown as SEQ ID NO:13.

(4) Construction of 3,4-AHBA Producing Bacteria

Competent cells of *Escherichia coli* BW25113 strain and BW25113 ΔnhoA strain were prepared, subsequently pSTV28-EcGri was introduced thereto by electroporation, then the cells were uniformly applied onto an LB plate containing 30 mg/L of chloramphenicol, and cultured at 37° C. for 24 hours. Transformants that were resistant to chloramphenicol were obtained from the resulting plate. pSTV28-EcGri was introduced into the BW25113 strain, and the resulting strain was designated as BW25113/pSTV28-EcGri strain, and pSTV28-EcGri was introduced into *Escherichia coli* BW25113 ΔnhoA strain, and the resulting strain was designated as BW25113ΔnhoA/pSTV28-EcGri strain.

(5) Evaluation of Cultivation for Producing 3,4-AHBA

Microbial cells of BW25113ΔnhoA/pSTV28-EcGri strain and BW25113/pSTV28-EcGri strain were uniformly applied onto an LB plate containing 30 mg/L of chloramphenicol, and cultured at 37° C. for 24 hours. One loopful of the microbial cells from the resulting plate was inoculated in 4 mL of MS glucose/Asp medium containing 30 mg/L of chloramphenicol and 0.1 mM isopropyl-β-thiogalactopyranoside in a test tube, and cultured at 30° C. for 48 hours on the reciprocal shaking cultivation apparatus. A composition of the MS glucose/Asp medium is as described in the following Table 3.

TABLE 3

Table 3. MS glucose/Asp medium

| Components | Final concentration (g/L) |
|---|---|
| Glucose | 40 |
| $(NH_4)_2SO_4$ | 24 |
| Aspartic acid | 5 |
| $KH_2PO_4$ | 1 |
| $MgSO_4 \cdot 7H_2O$ | 1 |
| $FeSO_4 \cdot 7H_2O$ | 0.01 |
| $MnSO_4 \cdot 7H_2O$ | 0.0082 |
| Yeast Extract | 2 |
| $CaCO_3$ | 50 |

The pH value of the medium was adjusted to 7.0 with KOH, and the medium was autoclaved at 120° C. for 20 minutes. Glucose and $MgSO_4 \cdot 7H_2O$ were mixed and sterilized separately. $CaCO_3$ was added after dry heat sterilization.

After the cultivation, the OD value of the culture medium at 600 nm was measured using the spectrophotometer (HITACHI U-2900). 3,4-AHBA and 3,4-AcAHBA were separated using the reverse phase column chromatography, and their concentrations were quantified (Suzuki et. al., (2006) J. Biol. Chem., 281, 36944-36951). The OD values at 600 nm in the culture medium and the concentrations of 3,4-AHBA and 3,4-AcAHBA in the cultured supernatant are shown in Table 4. In BW25113ΔnhoA/pSTV28-EcGri strain, no 3,4-AcAHBA was detected and the concentration of 3,4-AHBA was much higher than that in the control strain BW25113/pSTV28-EcGri.

TABLE 4

Table 4. Effect of nhoA deletion on amount of accumulated 3,4-AHBA and 3,4-AcAHBA

| strain name | OD (600 nm) | Concentration of 3,4-AHBA (g/L) | Concentration of 3,4-AcAHBA (g/L) |
|---|---|---|---|
| BW25113/pSTV28-EcGri | 30.2 ± 0.2 | 0.11 ± 0.02 | 0.26 ± 0.02 |
| BW25113ΔnhoA/pSTV28-EcGri | 30.5 ± 0.3 | 0.30 ± 0.03 | N.D. |

N.D.: not detected

Each value is a mean value in the cultivation in triplicate.

Example 3

Construction of Bacteria Producing 3,4-AHBA by Introducing 3,4-AHBA Synthetase Gene Group Derived from *Streptomyces murayamaensis* and Evaluation of Amounts of Accumulated 3,4-AHBA and 3,4-AcAHBA (1) Chemical Synthesis of nspI Gene and nspH Gene Corresponding to Codon Usage in *Escherichia coli*

It has been reported that the synthesis of 3,4-AHBA is catalyzed by a 3,4-AHBA synthetase group consisting of aldolase (convertible term: NspI; NCBI accession ID: BAJ08171.1) and 3,4-AHBA synthase (convertible term: NspH; NCBI accession ID: BAJ08172.1) in *Streptomyces murayamaensis* (Furusaki et. al., (1972) Isr. J. Chem., 10, 173-187), and sequences of the genes encoding these enzymes have been reported (Noguchi et. al., (2010) Nat. Chem. Biol., 6, 641-643). NspI is encoded by an nspI gene (GenBank accession no. AB530136, nucleotides 8730 to 9584; GI: 296784943). An amino acid sequence of the NspI protein and a nucleotide sequence of the nspI gene are shown as SEQ ID NO:14 and SEQ ID NO:15, respectively. NspH is encoded by an nspH gene (GenBank accession no. AB530136, nucleotides 9599 to 10702; GI: 296784944). An amino acid sequence of the NspH protein and a nucleotide sequence of the nspH gene are shown as SEQ ID NO:16 and SEQ ID NO:17, respectively.

In order to efficiently express the nspI gene and the nspH gene in *Escherichia coli*, a sequence was designed so as to correspond to the codon usage in *Escherichia coli* by changing the sequences of the nspI gene and the nspH gene and to express as an operon, and this sequence was designated as EcNspIH. A DNA fragment was chemically synthesized by adding an EcoRI restriction enzyme recognition sequence to the 5' terminus and a HindIII restriction enzyme recognition sequence to the 3' terminus of EcNspIH. EcNspIH, both termini of which the restriction enzyme recognition sequence had been added to, was digested with EcoRI and HindIII, and then cloned into pUC57 (supplied from GenScript) digested with the same restriction enzymes. The resulting vector was designated as pUC57-EcNsp.

(2) Construction of Plasmid for Expressing nspI Gene and nspH Gene (nspIH Gene)

An expression plasmid for expressing the nspI gene and the nspH gene in *Escherichia coli* was constructed using the following procedure. PCR was performed with pUC57-EcNsp as a template using synthesized oligonucleotides as primers and using PrimeStar GXL polymerase (supplied from Takara Bio Inc.). A reaction solution was prepared according to a composition attached to the kit, and a reaction at 98° C. for 10 seconds, 55° C. for 15 seconds and 68° C. for 150 seconds was performed in 30 cycles. As a result, a PCR product of about 2.1 kbp containing the EcNspIH gene fragment was obtained. Subsequently, the purified EcNspIH gene fragment and pSTV28-Ptac-Ttrp digested with SmaI (described in Example 2) were ligated using In-Fusion HD Cloning Kit (supplied from Clontech). The resulting plasmid for expressing the nspIH gene was designated as pSTV28-EcNsp.

(3) Construction of 3,4-AHBA Producing Bacteria

Competent cells of *Escherichia coli* BW25113 strain and BW25113 ΔnhoA strain were prepared, subsequently pSTV28-EcNsp was introduced thereto by electroporation, then the cells were uniformly applied onto an LB plate containing 30 mg/L of chloramphenicol, and cultured at 37° C. for 24 hours. Transformants that were resistant to chloramphenicol were obtained from the resulting plate. pSTV28-EcNsp was introduced into the BW25113 strain, and the resulting strain was designated as BW25113/pSTV28-EcNsp strain, and pSTV28-EcNsp was introduced into *Escherichia coli* BW25113 ΔnhoA strain, and the resulting strain was designated as BW25113ΔnhoA/pSTV28-EcNsp strain.

(4) Evaluation of Cultivation for Producing 3,4-AHBA

Microbial cells of BW25113/pSTV28-EcNsp strain and BW25113ΔnhoA/pSTV28-EcNsp strain were uniformly applied onto an LB plate containing 30 mg/L of chloramphenicol, and cultured at 37° C. for 24 hours. One loopful of the microbial cells from the resulting plate was inoculated in 4 mL of MS glucose/Asp medium containing 30 mg/L of chloramphenicol and 0.1 mM isopropyl-β-thiogalactopyranoside (see Table 3) in a test tube, and cultured at 30° C. for 48 hours on the reciprocal shaking cultivation apparatus.

After the cultivation, the OD value of the culture medium at 600 nm was measured using the spectrophotometer (HITACHI U-2900). 3,4-AHBA and 3,4-AcAHBA were separated using the reverse phase column chromatography, and their concentrations were quantified (Suzuki et. al., (2006) J. Biol. Chem., 281, 36944-36951). The OD values at 600 nm in the culture medium and the concentrations of 3,4-AHBA and 3,4-AcAHBA in the cultured supernatant were shown in Table 5. In BW25113ΔnhoA/pSTV28-EcNsp strain, no 3,4-AcAHBA was detected and the concentration of 3,4-AHBA was much higher than that in the control strain BW25113/pSTV28-EcNsp.

TABLE 5

Table 5. Effect of nhoA deletion on amount of accumulated 3,4-AHBA and 3,4-AcAHBA

| Strain name | OD (600 nm) | Concentration of 3,4-AHBA (g/L) | Concentration of 3,4-AcAHBA (g/L) |
|---|---|---|---|
| BW25113/pSTV28-EcNsp | 30.2 ± 0.5 | 0.17 ± 0.01 | 0.28 ± 0.03 |
| BW25113ΔnhoA/pSTV28-EcNsp | 31.5 ± 2.7 | 0.47 ± 0.02 | N.D. |

N.D.: not detected

Each value is a mean value in the cultivation in triplicate.

INDUSTRIAL APPLICABILITY

According to the present invention, it is possible to conveniently and inexpensively produce an amino-hydroxybenzoic acid-type compound that is useful as an intermediate in the manufacture of dyes, agricultural chemicals, pharmaceuticals and other organic synthesized articles and as a monomer for polybenzoxazole. Thus, for example, polybenzoxazole (PBO) is obtained by polymerizing 3-amino-4-hydroxybenzoic acid obtained by the present invention, thereby enabling to inexpensively provide PBO fibers and PBO films having high strength, high elastic modulus and high resistance to heat. It is also possible to produce a 3-amino-4-hydroxybenzoic acid-type compound that can be used as a raw material in various biosyntheses. Thus, the method of the present invention is a process with low environmental load and an environmentally-friendly production method.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing a 3-amino-4-hydroxybenzoic acid or a salt thereof, comprising a step of culturing an *Escherichia coli* bacterium having an ability to produce 3-amino-4-hydroxybenzoic acid which has been genetically modified to express DNA which encodes an enzyme to increase the activity of an enzyme, wherein said enzyme is capable of catalyzing formation of 3-amino-4-hydroxybenzoic acid from dihydroxyacetone phosphate and aspartate semialdehyde as compared to a non-modified *Escherichia coli* bacterium, and wherein said enzyme is GriI and GriH; and wherein the *Escherichia coli* bacterium also has been modified to inactivate an N-hydroxyarylamine O-acetyltransferase (NhoA) as compared to a non-modified *Escherichia coli* bacterium by mutating or deleting an nhoA gene on the chromosome of the *Escherichia coli* bacterium.

2. The method according to claim 1, further comprising a step of polymerizing the 3-amino-4-hydroxybenzoic acid.

3. The method according to claim 2, wherein the polymer is a polybenzoxazole polymer.

4. The method according to claim 1, wherein the GriI is a protein selected from the group consisting of:
(A) a protein comprising the amino acid sequence represented by SEQ ID NO:5 or SEQ ID NO: 14;
(B) a protein comprising an amino acid sequence having 1 to 10 amino acid substitutions, deletions, insertions or additions in the amino acid sequence shown in (A) above, and having an aldolase activity; and
(C) a protein comprising an amino acid sequence having 95% or more identity to the amino acid sequence represented in (A) above and having an aldolase activity;

and the GriH is a protein selected from the group consisting of:
(D) a protein comprising the amino acid sequence represented by SEQ ID NO:7 or SEQ ID NO: 16;
(E) a protein comprising an amino acid sequence having 1 to 10 amino acid substitutions, deletions, insertions or additions in the amino acid sequence shown in (D) above, and having a 3-amino-4-hydroxybenzoic acid synthase activity; and
(F) a protein comprising an amino acid sequence having 95% or more identity to the amino acid sequence shown in (D) above and having a 3-amino-4-hydroxybenzoic acid synthase activity.

5. The method according to claim 1, wherein said DNA comprises a griI gene and a griH gene.

6. The method according to claim 5, wherein the griI gene is selected from the group consisting of:
(a) a DNA comprising the nucleotide sequence represented by SEQ ID NO:6 or SEQ ID NO: 15;
(b) a DNA that hybridizes under a stringent condition with the nucleotide sequence complementary to the nucleotide sequence shown in (a) above and encodes a protein having an aldolase activity; and
(c) a DNA having 95% or more identity to the nucleotide sequence shown in (a) above and encoding a protein having an aldolase activity;

and the griH gene is selected from the group consisting of:
(d) a DNA comprising the nucleotide sequence represented by SEQ ID NO:8 or SEQ ID NO: 17;
(e) a DNA that hybridizes under a stringent condition with the nucleotide sequence complementary to the nucleotide sequence shown in (d) above and encodes a protein having a 3-amino-4-hydroxybenzoic acid synthase activity; and
(f) a DNA having 95% or more identity to the nucleotide sequence shown in (d) above and encoding a protein having a 3-amino-4-hydroxybenzoic acid synthase activity;
wherein said stringent condition of (b) and (e) above comprises hybridization in 6×SSC at about 45° C. followed by washing once, twice, or more times in 0.2×SSC and 0.1% SDS at 50 to 65° C.

7. The method according to claim 6, wherein the griI gene and the griH gene are from an actinomycete.

8. The method according to claim 6, wherein the griI gene and the griH gene are from the genus *Streptomyces*.

9. The method according to claim 6, wherein the griI gene and the griH gene are from *Streptomyces griseus*.

10. The method according to claim 6, wherein the griI gene and the griH gene are from *Streptomyces murayamaensis*.

11. The method according to claim 1, having wherein said *Escherichia coli* bacterium also has a gene encoding a mutated aspartokinase III in which feedback inhibition is canceled.

* * * * *